(12) United States Patent
Kool et al.

(10) Patent No.: US 6,773,587 B2
(45) Date of Patent: Aug. 10, 2004

(54) POINT-OF-USE WATER TREATMENT SYSTEM

(75) Inventors: Dennis J. Kool, Kentwood, MI (US); James A. Woodard, Jr., Powell, OH (US); Rick G. Good, Rockford, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 10/234,623

(22) Filed: Sep. 4, 2002

(65) Prior Publication Data

US 2003/0000880 A1 Jan. 2, 2003

Related U.S. Application Data

(60) Division of application No. 09/744,844, filed as application No. PCT/US99/17374 on Jul. 30, 1999, now Pat. No. 6,533,930, which is a continuation-in-part of application No. 09/299,053, filed on Apr. 23, 1999, now Pat. No. 6,245,229.
(60) Provisional application No. 60/094,918, filed on Jul. 31, 1998.

(51) Int. Cl.[7] .............................. C02F 1/32; C02F 9/12; C02F 1/28; C02F 35/30
(52) U.S. Cl. .................... 210/232; 210/198.1; 210/748; 210/259; 210/260; 210/205; 210/175; 210/238; 210/541; 422/24; 422/186.3
(58) Field of Search ............... 210/232, 198.1, 210/748, 259, 260, 205; 422/186.3

(56) References Cited

U.S. PATENT DOCUMENTS

| | | |
|---|---|---|
| 1,918,980 A | 7/1933 | Nugent |
| 3,413,465 A | 11/1968 | Harrison et al. |
| 3,510,641 A | 5/1970 | Reynolds |
| 3,633,748 A | 1/1972 | Hanley |
| 3,710,047 A | 1/1973 | Brzozowski et al. |
| 3,739,319 A | 6/1973 | Garnett |
| 3,950,251 A | 4/1976 | Hiller |
| 4,008,045 A | 2/1977 | Free |
| 4,156,652 A | 5/1979 | Wiest |
| 4,267,455 A | 5/1981 | Keller |
| 4,419,234 A | 12/1983 | Miller et al. |
| 4,465,595 A | 8/1984 | Cooper |
| 4,467,930 A | 8/1984 | Schnell et al. |
| 4,476,015 A | * 10/1984 | Schmitt et al. ............... 210/93 |
| 4,495,072 A | 1/1985 | Fields |
| 4,659,466 A | 4/1987 | Farr et al. |
| 4,694,179 A | * 9/1987 | Lew et al. .................. 250/431 |

(List continued on next page.)

FOREIGN PATENT DOCUMENTS

| | | |
|---|---|---|
| EP | 0201154 | 12/1986 |
| GB | 2267635 | 8/1993 |
| GB | 2315261 | 1/1996 |
| WO | WO9708099 | 3/1997 |

Primary Examiner—Thomas M. Lithgow
(74) Attorney, Agent, or Firm—Warner Norcross & Judd LLP

(57) ABSTRACT

The present invention relates to a point-of-use water treatment system unit (10). The unit (10) includes a filter housing assembly (60) having a filter tank assembly (66) and a closure (64) which utilizes a handle (152) and cammed reciprocating lock blades (146, 150) to secure the closure (64) to the filter tank assembly (66). A UV tank assembly (300) includes a planar baffle plate (322) and a vaned baffle plate (324) to induce plug flow about a UV lamp assembly (280). The UV lamp assembly (280) is used which simultaneously electrically and sealingly mounts to UV tank assembly (300) and electrical cap assembly (290) using a bayonet mount. A bi-planar manifold assembly (40) is used to interconnect components of the WTS unit and to provide an envelope for accommodating a water pipe assembly (34). The bi-planar manifold assembly (40) enhances the compactness of the design of the WTS unit (10). Also, a support plate (26) is disclosed which provides support to subcomponents of the WTS unit (10) while also dissipating heat from a UV tank assembly (300).

8 Claims, 22 Drawing Sheets

U.S. PATENT DOCUMENTS

| | | | |
|---|---|---|---|
| 4,713,175 A | 12/1987 | Bray | |
| 4,818,398 A | 4/1989 | Lott et al. | |
| 4,902,411 A | 2/1990 | Lin | |
| 4,909,931 A | 3/1990 | Bibi | |
| 4,971,687 A | 11/1990 | Anderson | |
| 5,068,030 A | 11/1991 | Chen | |
| 5,128,035 A * | 7/1992 | Clack et al. | 210/251 |
| 5,133,945 A | 7/1992 | Hallett | |
| 5,143,601 A * | 9/1992 | Slovak et al. | 210/90 |
| 5,209,845 A | 5/1993 | Sims | |
| 5,227,053 A | 7/1993 | Byrm | |
| 5,227,637 A | 7/1993 | Herold et al. | |
| 5,254,242 A | 10/1993 | van der Meer et al. | |
| 5,266,215 A | 11/1993 | Engelhard | |
| 5,266,280 A | 11/1993 | Hallett | |
| 5,372,781 A | 12/1994 | Hallett et al. | |
| 5,394,601 A | 3/1995 | Sutton et al. | |
| 5,422,487 A | 6/1995 | Sauska et al. | |
| 5,451,791 A | 9/1995 | Mark | |
| 5,456,830 A | 10/1995 | Stanford et al. | |
| 5,505,912 A | 4/1996 | Hallett | |
| 5,514,275 A | 5/1996 | Morgan, Jr. | |
| 5,529,689 A | 6/1996 | Korin | |
| 5,536,395 A | 7/1996 | Kuennen et al. | |
| 5,540,848 A | 7/1996 | Engelhard | |
| 5,573,666 A | 11/1996 | Korin | |
| 5,597,482 A | 1/1997 | Melyon | |
| 5,624,559 A | 4/1997 | Levin et al. | |
| 5,660,802 A | 8/1997 | Archer et al. | |
| 5,675,153 A | 10/1997 | Snowball | |
| 5,696,380 A | 12/1997 | Cooke et al. | |
| 5,698,091 A | 12/1997 | Kuennen et al. | |
| 5,753,996 A | 5/1998 | Csoknyai | |
| 5,785,845 A | 7/1998 | Colaiano | |
| 5,833,740 A | 11/1998 | Brais | |
| 5,843,309 A | 12/1998 | Mancil | |
| 5,853,572 A | 12/1998 | Kuennen et al. | |
| 6,080,313 A * | 6/2000 | Kelada | 210/631 |

* cited by examiner

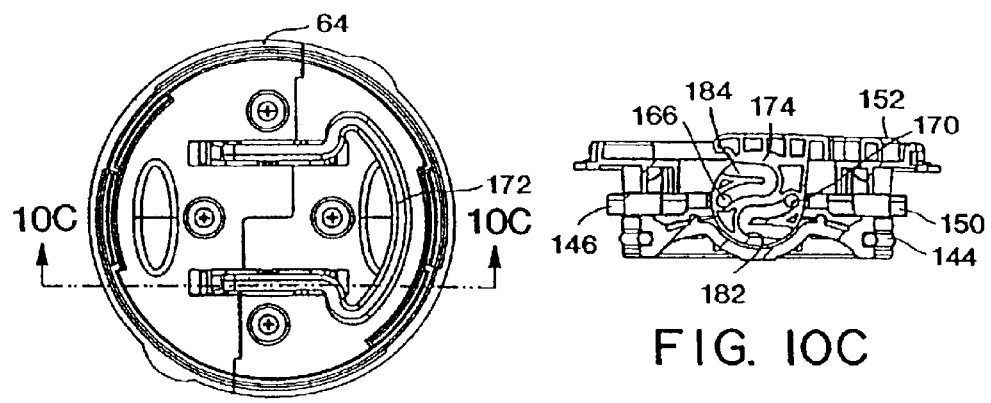
FIG. 10A
FIG. 10C
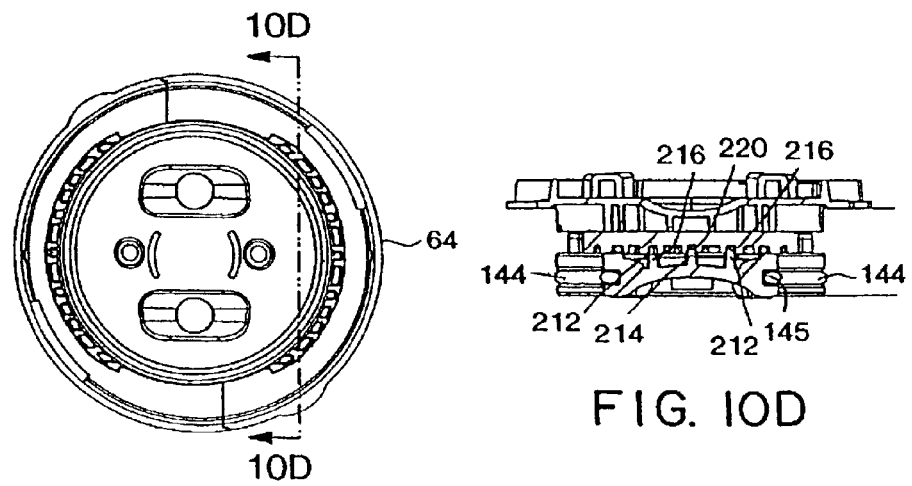
FIG. 10B
FIG. 10D

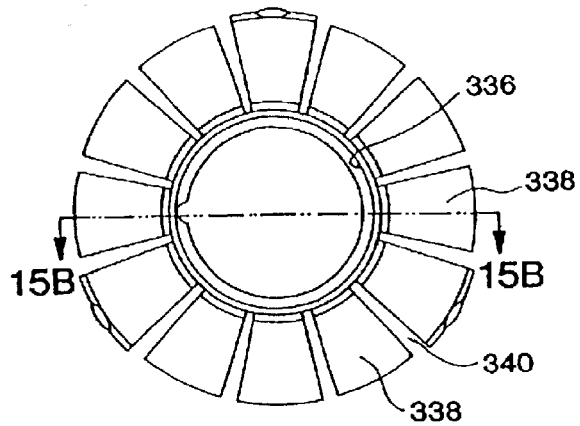
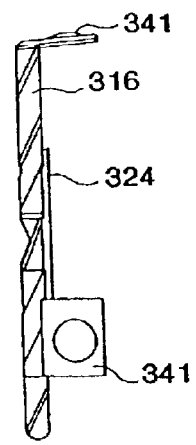
FIG. 15A
FIG. 15C
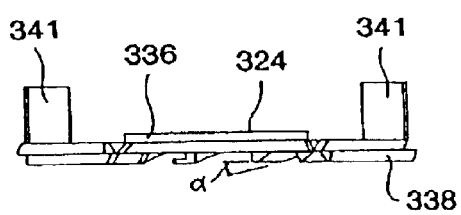
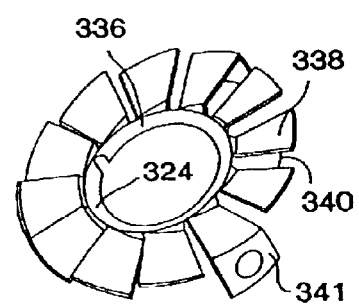
FIG. 15B
FIG. 15D

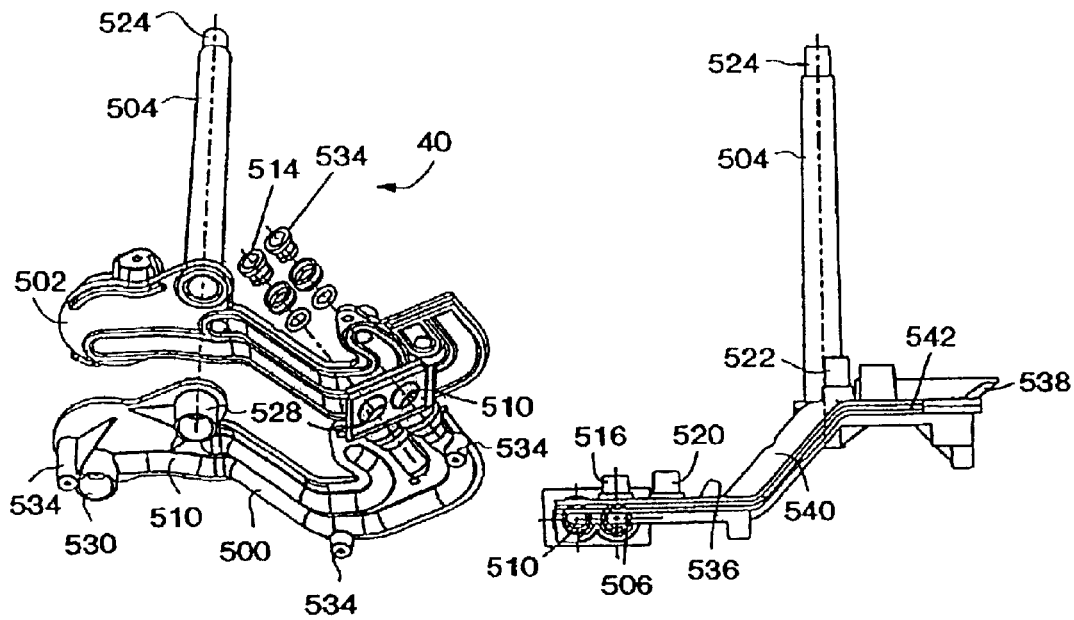
FIG. 19A
FIG. 19B
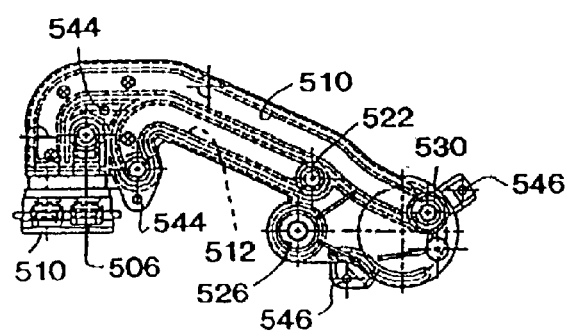
FIG. 19C
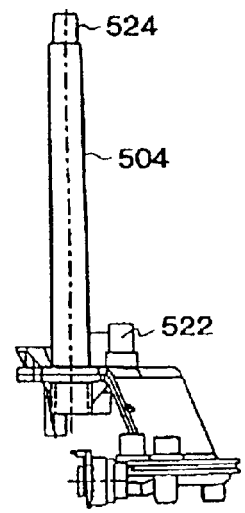
FIG. 19D

POINT-OF-USE WATER TREATMENT SYSTEM

This is a division of U.S. application Ser. No. 09/744,844, filed Jan. 30, 2001 (now U.S. Pat. No. 6,553,930), which is the National Stage of International PCT Application No. PCT/US99/17374, filed Jul. 30, 1999, which was published in English under PCT Article 21(2), which claims benefit to U.S. Provisional Application No. 60/094,918; filed Jul. 31, 1998, and which is a continuation-in-part of U.S. application Ser. No. 09/299,053, filed Apr. 23, 1999, now U.S. Pat. No. 6,245,229.

TECHNICAL FIELD

The present invention relates to point-of-use water treatment system (WTS) units for above or below countertop use in homes or offices for the purposes of removing contaminants from water.

BACKGROUND OF THE INVENTION

The present invention minimizes or overcomes several problems associated with previous point-of-use home or office water treatment system (WTS) units. These WTS units are often connected to a faucet using a faucet diverter valve assembly. Water can be supplied directly from the faucet, or using the faucet diverter valve assembly, can be routed through a WTS unit for removal of contaminants prior to being dispensed from a faucet. The WTS units often include a carbon block filter to remove particulates, an ultraviolet (UV) bulb for destroying microorganisms found in water, and a flow meter to monitor the quantity of water treated over a specified period of time.

A first problem many WTS units encounter is that filter closures can be difficult to remove from or install on WTS unit filter housings. This is particularly true of closures that rely upon threaded connections. The closures combine with the filter housings to form closed pressure vessels in which filters are stored. The diameters of filters are ideally as large as possible to increase the capacity and life expectancy of the filters. Similarly, the diameter of filter housings must be large to accommodate the filters. Conventional threaded connections between the filter closures and filter housings, which are both usually made of plastic, often "weld" together. This phenomenon is known as galling. The "welding" action is partially attributable to the long period of time between filter changes and also to the wet and warm environment in which WTS units operate.

WTS units often include a UV (ultraviolet) bulb for destroying microorganisms in the water to be treated. These UV bulbs typically operate continuously. After water has not been run through a WTS unit for a significant period of time, such as overnight, heat from the UV bulb and other electrical circuitry can cause heat to build up inside and elevate the temperature of water stored within the WTS unit. The resulting increased temperature contributes to plastic creep and the "welding" together of the threads on the filter closure and filter housing. Because of the large area of contact between the threads, considerable force may be required to break the "weld" on the threads and release the closure from the filter housing.

Alternatively, some WTS units use bayonet mounted filter closures. A problem with this type of mount is that a filter closure must be accurately aligned with a housing to effect mounting of the filter closure to the filter housing. Also, even with a bayonet mount, there is still significant joint contact area between the filter closure and the filter housing. Again, significant force may be required to break the filter closure free from the filter housing after a long period of attachment.

A second problem associated with WTS units having UV bulbs is the build up of heat within the WTS units. Adverse consequences related to elevated temperature include structural degradation of plastic components over time due to creep, discoloration of plastic components, and decreased reliability of electrical circuitry. Also, the temperature of water stored overnight within a WTS unit can become uncomfortably warm to the touch when discharged from the WTS unit. Therefore, it is beneficial for a WTS unit to be designed to minimize its internal heat buildup.

Further, most WTS units use plastic molded decorative outer housings to enclose internal components. These plastic outer housings decrease in strength as temperature increases. If the WTS unit is to be wall mounted and must rely solely upon the strength of the outer housing, then the outer housing must be relatively thick, made of high strength plastic and resistant to creep induced by high temperatures and mechanical loads. Accordingly, expensive specialty plastics may be required in making such outer housings.

A third problem associated with WTS units having UV bulbs is that UV bulbs are cumbersome to change. The UV bulbs have a limited lifetime and must be periodically changed. While the UV light emitted by the bulbs is beneficial in destroying chemical bonds in microorganisms, hence severely inhibiting their ability to replicate or reproduce, the UV light can also be harmful to human eyes. Consequently, the UV bulbs must be mounted without UV light exposure to the installer. Often this requires numerous steps such as connecting a UV bulb to a power source, closing a housing about the UV bulb to prevent UV light exposure, and then energizing the UV bulb to insure that the UV bulb will properly operate. Ideally, a UV bulb could be easily and quickly installed with the UV bulb immediately lighting upon installation to show that it is operating properly while preventing direct exposure of the UV light to the operator.

A fourth problem common to WTS units having UV light disinfection is that water flowing through a UV tank assembly may not be uniformly treated or exposed to UV light. A UV bulb is typically mounted in a UV tank assembly with water passing around the UV bulb. All portions of the water should receive a predetermined minimal exposure or dosage of UV light. Depending on how the water is directed through the UV tank assembly, portions of the water flow receive lesser or greater amounts of exposure. That is, portions of water that pass most quickly through the UV tank assembly tend to receive less UV light exposure than portions of water that take a slower path and have a longer residence time. Ideally, all the water would receive the same predetermined minimum dosage of UV light to ensure a desired kill or destruction rate without unnecessarily overexposing certain portions of the water flow. Without steady or plug flow through the UV tank assembly, this objective cannot be optimally met. Plug flow refers to a "plug" or mass of water moving together through the system. Plug flow avoids uneven flow rate of water through the system.

Some WTS units utilize water transporting Teflon coils surrounding a UV bulb to achieve a generally uniform flow rate for all water. However, the Teflon coils can deteriorate and/or cloud over. Also, the Teflon coils can be damaged by heat. Further, water borne contaminants may reduce the transmissibility of light through the Teflon coils over time. Therefore, the coils must be cleaned or replaced in certain water conditions.

One example of a UV tank assembly that addresses this problem is shown in U.S. Pat. No. 5,536,395. A tank includes a generally cylindrical main portion and a reduced diameter neck portion. The cylindrical portion has attached thereto an inlet and a coaxially aligned annular baffle plate with circular openings therein. Water enters the inlet inducing circumferential water flow and then passes through the openings in the baffle plate. As a result, water flowing downstream from the annular baffle plate travels in a generally spiral motion about a UV bulb disposed within the UV tank assembly. The water then passes to the reduced neck portion before exiting the tank through an outlet fitting. While this UV tank assembly design provides satisfactory flow characteristics, the tank is expensive and difficult to manufacture due to numerous deep drawing operations required to form the tank. Further, there are numerous machining operations which must be performed on stainless steel components which also increases the complexity and cost of manufacture.

Another drawback conventional WTS units have is the use of a plurality of tubes to fluidly interconnect the various components of the WTS units. Individual tubes are typically used to interconnect inlets, outlets, UV subassemblies and filter subassemblies and flow monitoring devices. The large number of tubes used makes assembly inconvenient and time consuming. Further, tubes can become brittle over time and may eventually have to be replaced. With this complexity of tubes and tube clamps, replacement of parts is difficult for the average consumer. Also, as the tubes are non-structural members, additional supporting members must be used to support components such as flow meters and UV and filter subassemblies apart from support provided by decorative housings of the WTS units. Moreover, designs utilizing tubes makes optimization of the compactness of a WTS unit difficult.

The present invention includes designs and features which overcome, or at least minimize, many of the problems identified above which are encountered by previous water treatment system units.

SUMMARY OF THE INVENTION

The present invention includes a WTS unit which has a unique filter closure and attachment mechanism that allows the closure to be easily and quickly secured to and removed from a filter housing. The filter housing has a filter chamber for receiving a filter. The closure releasably seals with the housing assembly to form a closed pressure vessel. The attachment mechanism is ideally attached to the closure and utilizes a mechanical advantage, preferably in the form of a pivoting handle which cams a pair of reciprocating lock blades into and out of engagement with one or more blade receiving openings on the filter housing.

The present invention also covers a WTS unit having a UV tank assembly, a UV bulb assembly received within the UV tank, and a heat dissipating support plate juxtaposed the UV tank assembly. This arrangement allows heat generated by the UV bulb assembly and transferred to the UV tank to be readily transferable to the support plate and then the atmosphere. Use of the heat dissipating support plate also allows low strength decorative outer housing components to be used with the WTS unit as the support plate provide structural support to internal components and for wall mounting of the WTS unit.

A point-of-use water treatment system is disclosed having a base, a UV tank assembly, an electrical connector cap assembly and a UV lamp assembly. The cap assembly attaches to the UV tank assembly. The UV lamp assembly simultaneously mounts to the cap assembly and UV tank assembly to form a closed pressure vessel and to electrically communicate with the cap assembly. Ideally, a fluid seal is created between the UV lamp assembly and the tank assembly while the UV lamp assembly bayonet mounts to the cap assembly to create electrical communication therebetween. Further, the UV bulb assembly preferably includes a light pipe which is visible from the exterior of the WTS unit to indicate when the UV lamp assembly is operating.

A UV tank assembly is provided which includes a generally cylindrical sleeve and first and second longitudinally spaced apart annular baffle plates. The first baffle plate is ideally planar and has a plurality of openings therein. The second baffle plate is preferably vaned. When a UV lamp assembly is placed within the UV tank assembly, water flowing from the first baffle plate to the second baffle plate travels in a spiral path about a UV bulb providing the water generally uniform exposure to UV light. This particular UV tank assembly is relatively simple in construction and inexpensive to manufacture.

The invention further includes a WTS unit having a UV subsystem, a filter subsystem, a flow monitor, a base and a bi-planar manifold. The manifold has first and second halves which are joined together to cooperatively provide conduits which fluidly interconnect the filter subsystem, the UV subsystem and the flow monitor. The filter subsystem rests upon a first plane of the manifold and the UV subsystem rests upon a second elevated plane of the manifold with the flow monitor being positioned in an envelope created beneath the second plane of the manifold and the base of the WTS unit. This arrangement allows for a compact design for the WTS unit.

It is an object of the present invention to provide a WTS unit which has a filter closure which is easily installed on and removed from a filter housing even after the filter closure has been mounted to the fitter housing for an extended period of time.

Another object is to provide a filter closure having an attachment mechanism which utilizes a mechanical advantage such that undue force or strength is not required by a user to effect removal of the filter closure.

An additional object is to provide a high thermal conductivity and high strength support plate to support major components of a WTS unit while enhancing heat dissipation from the WTS unit.

Yet another object is to provide a WTS unit having a UV lamp assembly which allows a UV bulb, in a single quick movement, to be concurrently electrically connected to a power supply while fluidly sealing with a UV tank assembly thereby eliminating exposure of UV light to a WTS unit user. This eliminates the extra step of locating and attaching a wiring harness to complete assembly.

Another object is to provide a UV tank assembly which is inexpensive to manufacture yet cooperates with a UV bulb to allow generally uniform flow and UV light exposure to water passing by the UV bulb.

Still a further object is to provide a WTS unit having a bi-planar manifold assembly which interconnects with the major components of the WTS unit to provide simple yet reliable fluid connections therebetween. The manifold assembly provides structural support to other subcomponents and partially defines an envelope for placing a flow meter and monitor assembly.

Another object is to provide a WTS unit having a UV bulb assembly with a light pipe thereon, the light pipe being replaceable with the UV bulb assembly and extending through an opening in the outer housing of the WTS unit to indicate when a UV bulb is operating.

BRIEF DESCRIPTION OF THE DRAWINGS

These and other features, objects, and advantages of the present invention will become readily apparent from the following description, pending claims, and accompanying sheets of drawings where:

FIGS. 10A–D are, respectively, a top plan view, a bottom plan view, a sectional view taken along line 10C—10C of FIG. 1A, and a sectional view taken along line 10D—10D of FIG. 10B;

FIGS. 15A–D are a top plan view, an elevational view, a rotated elevational view and a perspective view of a vaned baffle plate utilized in the UV tank assembly;

FIGS. 19A–F are an exploded perspective view, an elevational view, a bottom plan view, a left side view, an upper perspective view, including a heat dissipating support plate, and a lower perspective view, including the support plate, of a manifold assembly.

BEST MODE(S) FOR CARRYING OUT THE INVENTION

Figure 1:
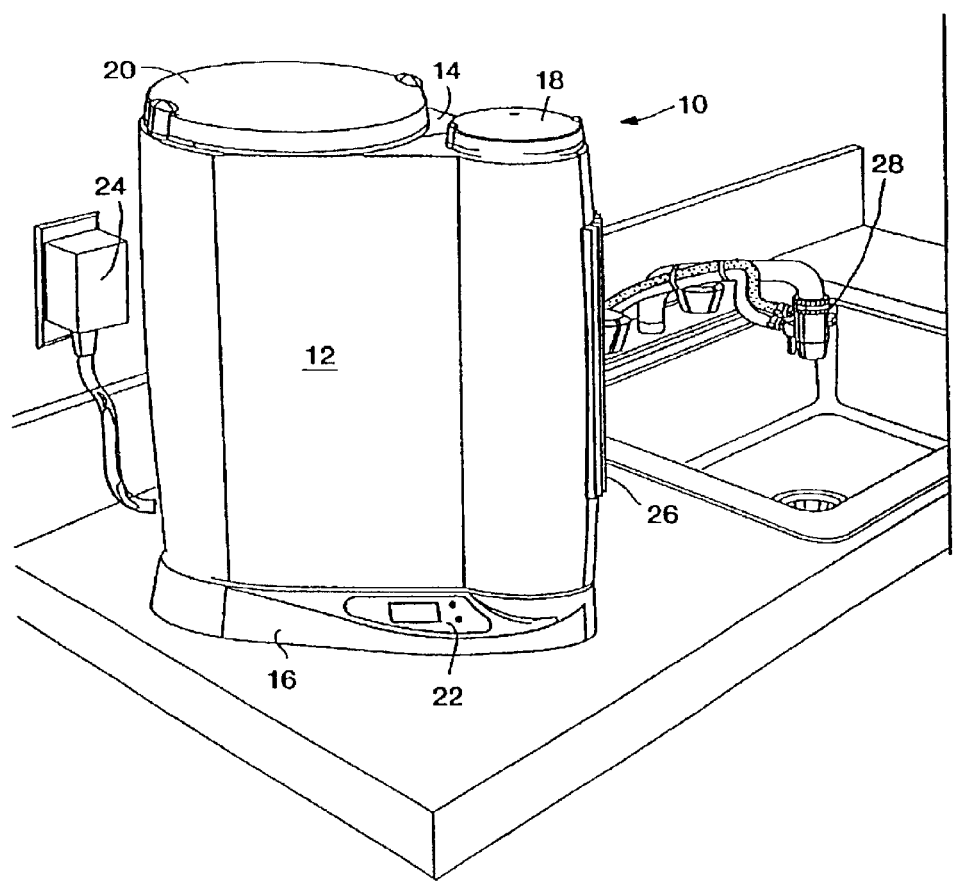
FIG. 1 is a perspective view of a WTS unit, made in accordance with the present invention, connected to a faucet using a faucet diverter valve assembly.
Figure 2:
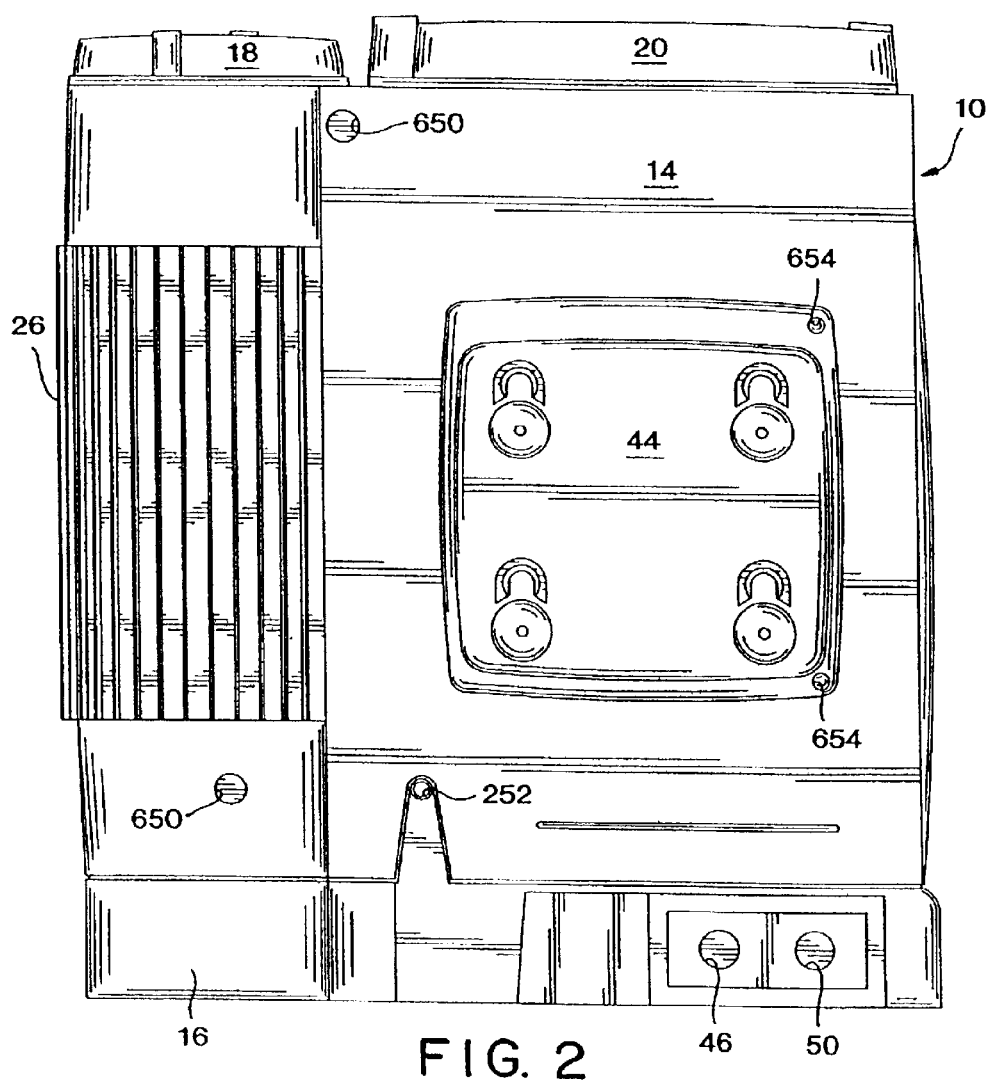
FIG. 2 is a rear elevational view of the WTS unit.

FIGS. 1 and 2 show a WTS (water treatment system) unit 10 made in accordance with the present invention. WTS unit 10 uses carbon block filtration to filter particles and remove certain chemical contaminants from water. A UV light system is employed to destroy microorganisms. A monitor is used to report on the status of the filtration and the UV light systems.

WTS unit 10 includes a front outer housing 12, a rear outer housing 14, and a flow monitor assembly 16 which also serves as the base for the WTS unit 10. Located atop front and rear outer housings 12 and 14 are decorative bulb and filter covers 18 and 20. A monitor 22 is mounted in flow monitor assembly 16 which will be further described below. A power supply 24, In the form of a transformer, provides electrical power to WTS unit 10. A finned aluminum support plate 26 extends through an opening in rear outer housing 14 and facilitates the dissipation of heat from within WTS unit 10. A faucet diverter valve assembly 28 routes water to and from WTS unit 10.

Figure 3:
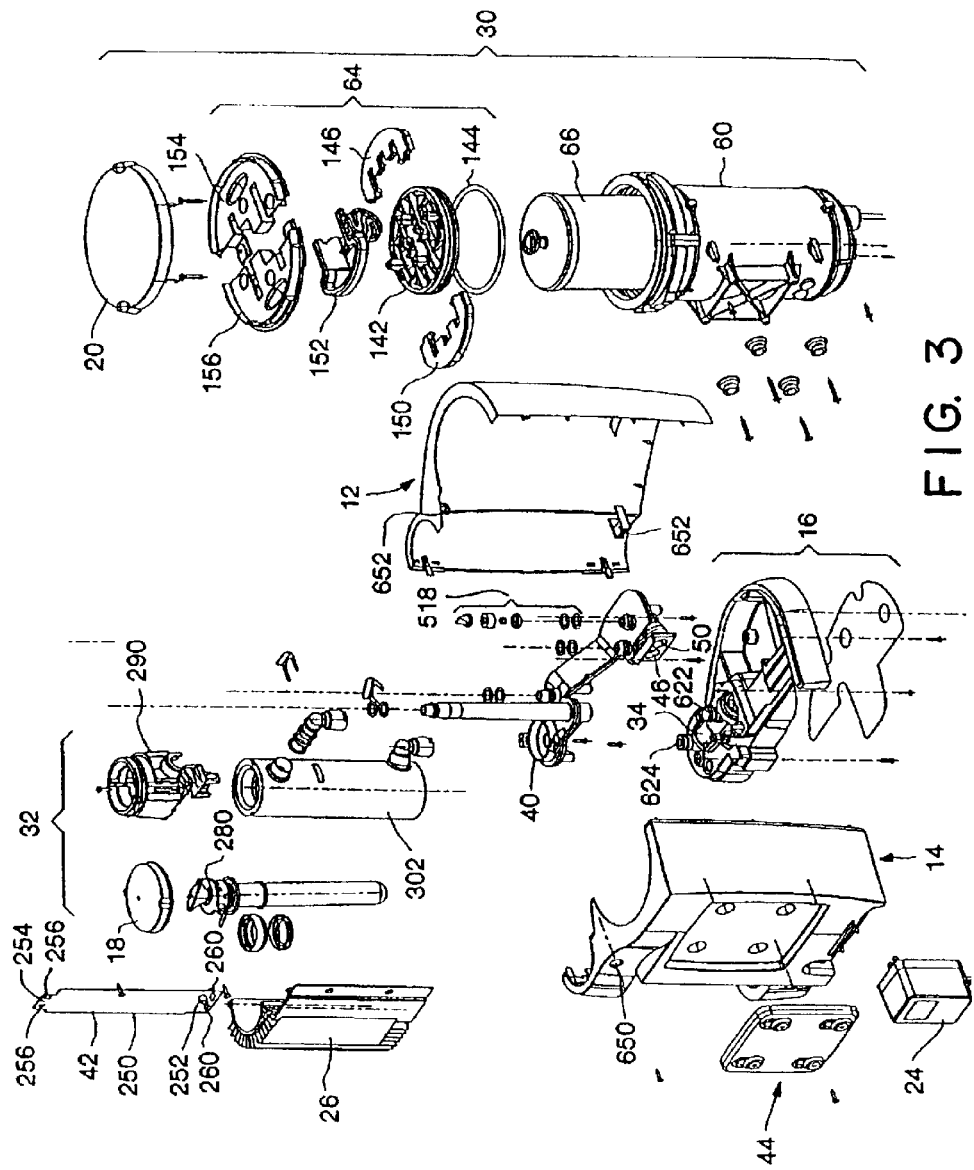
FIG. 3 is an exploded perspective view of major subcomponents of the WTS unit.
Figure 4:
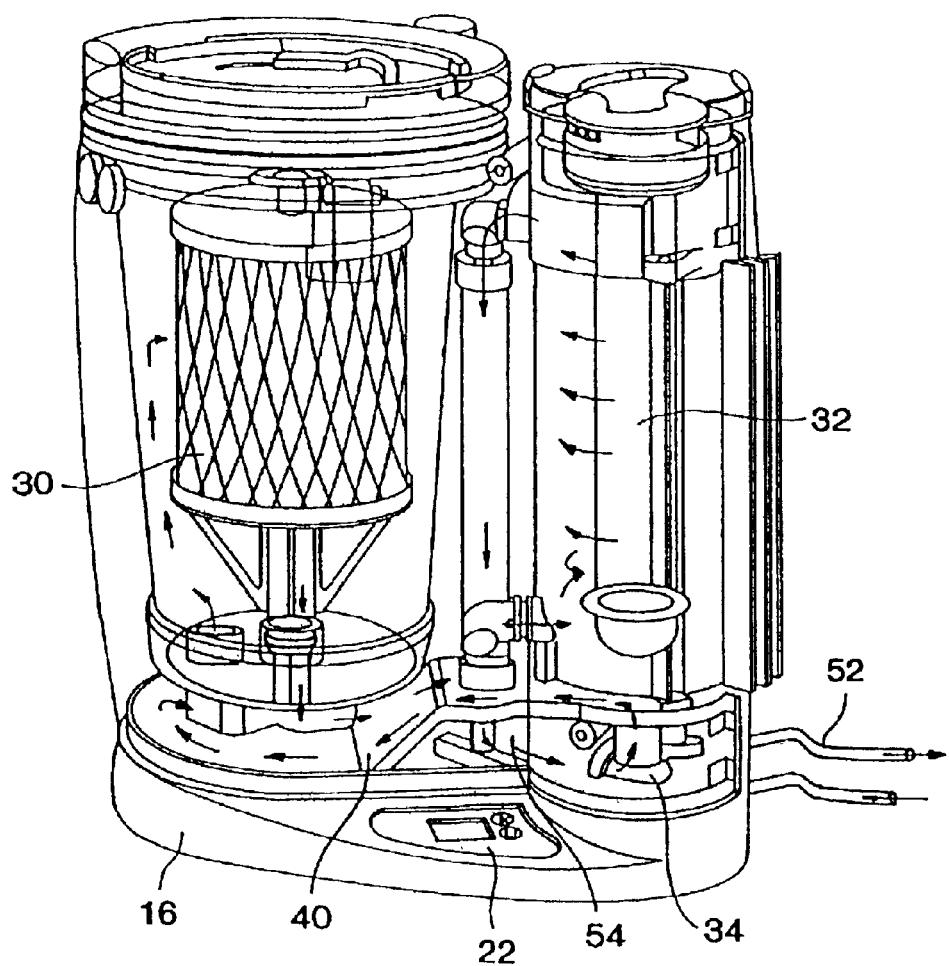
FIG. 4 is a fragmentary skeletal perspective view of the WTS unit.

Major subcomponents comprising WTS unit 10 are shown in an exploded perspective view in FIG. 3 and in skeletal perspective view in FIG. 4. These subcomponents include front outer housing 12, rear outer housing 14, flow monitor assembly 16, support plate 26, a filter subsystem 30, a UV subsystem 32, a water pipe assembly 34 mounted in flow monitor assembly 16, a manifold assembly 40, a PC board 42 and a wall mounting bracket 44. Manifold assembly 40 has an inlet 46 and an outlet 50 which connect to hoses 52 of faucet diverter valve assembly 28. Manifold assembly 40 fluidly interconnects with filter subsystem 30, UV subsystem 32 and water pipe assembly 34. An envelope 54, as best seen in FIG. 4, is formed beneath a portion of manifold 40 and above flow monitor assembly 16 to accommodate monitor 22 and water pipe assembly 34.

As a quick overview of the water flow path through WTS unit 10, water from faucet diverter valve assembly 28 is introduced into inlet 46 of manifold assembly 40. The water then travels from manifold assembly 40 to filter subsystem 30 for carbon block filtration. The filtered water is then discharged from filter subsystem 30 back to manifold assembly 40. Manifold assembly 40 delivers the filtered water to UV subsystem 32 for microorganism destruction by exposure to UV light. The filtered and disinfected water then leaves UV subsystem 32 and passes through water pipe assembly 34. The water finally returns to manifold assembly 40 and exits manifold outlet 50 and returns back to faucet diverter valve assembly 28.

Figure 5:
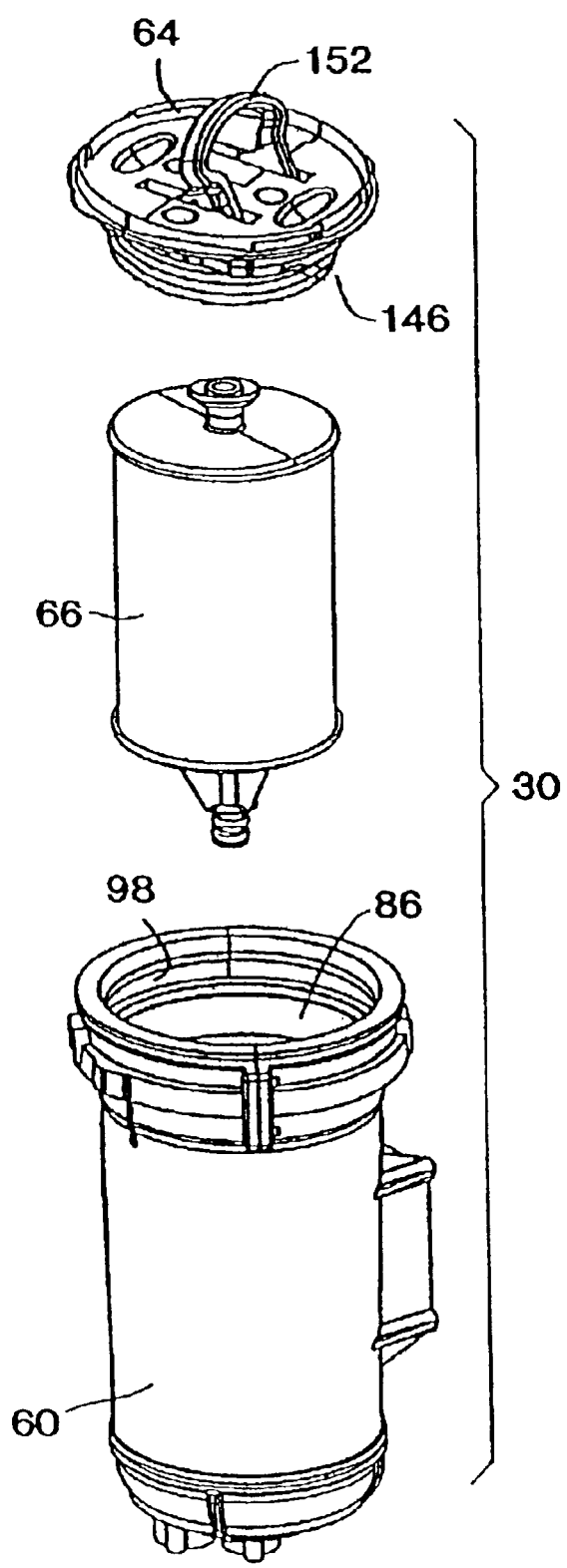
FIG. 5 is an exploded view of a filter housing assembly and filter block assembly.

Filter subsystem 30 is shown in exploded perspective view in FIGS. 3, 5 and 6. Components include a filter housing assembly 60, a closure or filter cap assembly 64 and a filter assembly 66. Filter assembly 66 is retained within filter housing assembly 60. Filter cap assembly 64 has a cammed closure and sealingly cooperates with filter housing assembly 60 to form a closed pressure vessel in which water is filtered through filter assembly 66.

Figure 6C:
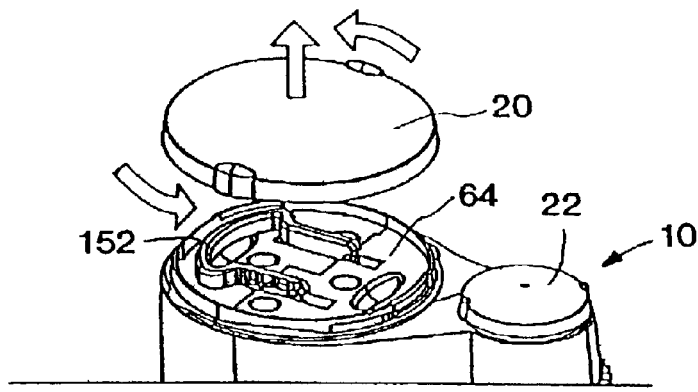
FIGS. 6A–C are fragmentary perspective views showing a filter block assembly being removed from the WTS unit.
Figure 6B:
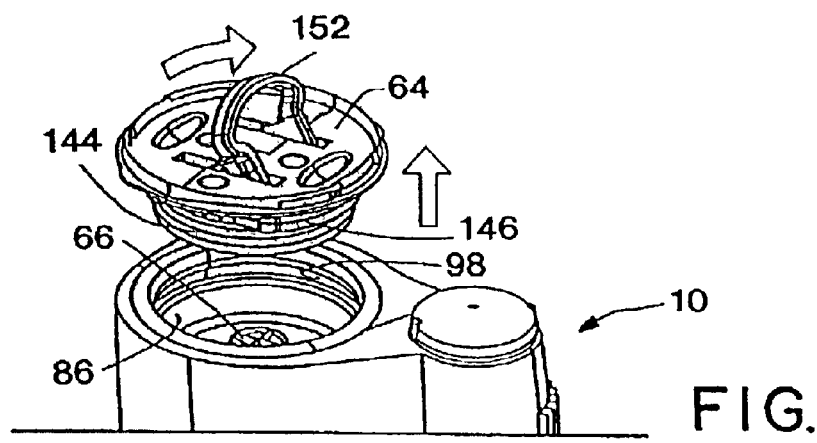
Figure 6A:
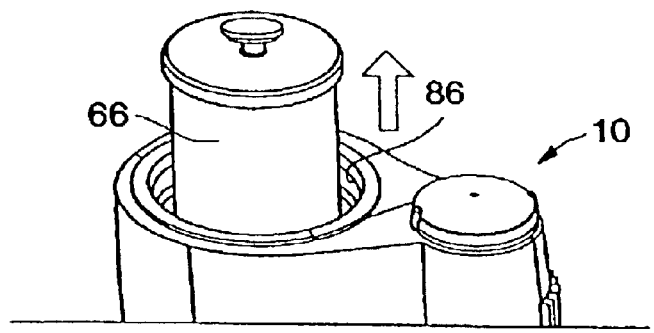

FIGS. 6A–C illustrate the removal of filter assembly 66 from WTS unit 10. Decorative filter cover 20 is rotated a quarter turn and is removed by unthreading from filter cap assembly 64. Next, a handle 152 on filter cap assembly 64 is pivoted upwardly causing a pair of reciprocating lock blades 146, 150 (not shown) to release radially inwardly from a circumferentially extending blade receiving groove 98 formed in a seal mating mouth 86 of filter housing assembly 60. Filter cap assembly 64 is lifted upwardly breaking a seal between filter cap assembly 64, an elastomeric O-ring 144 mounted on filter cap assembly 64, and seal mating mouth 86 on filter housing assembly 60. Filter assembly 66 is next lifted from filter housing assembly 60. A new filter assembly 66 can then be placed in filter housing assembly 60. Filter cap assembly 64 is pressed down into seal mating mouth 86 of filter housing assembly 60 reestablishing a seal therebetween utilizing O-ring 144. Filter cap assembly 64 is then locked in place by lowering handle 152 to a horizontal position which extends lock blades 146, 150 into blade receiving groove 98. Filter cover 20 is then reattached atop filter cap assembly 64. Handle 152 provides a significant mechanical advantage in reciprocating lock blades 146, 150 into and out of engagement with blade receiving groove 98, as will be described in greater detail below.

Figure 7A:
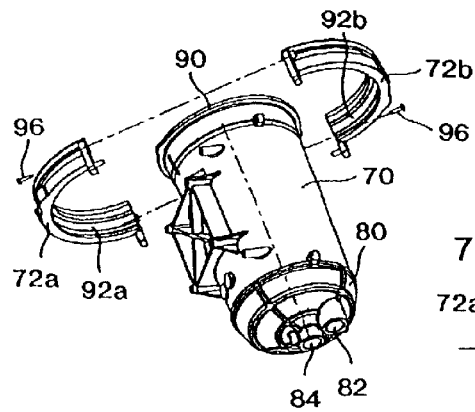
FIGS. 7A–D are, respectively, an exploded perspective view, a rear elevational view, a bottom plan view and a sectional view taken along line 7D—7D of FIG. 7C of a filter tank assembly.
Figure 7C:
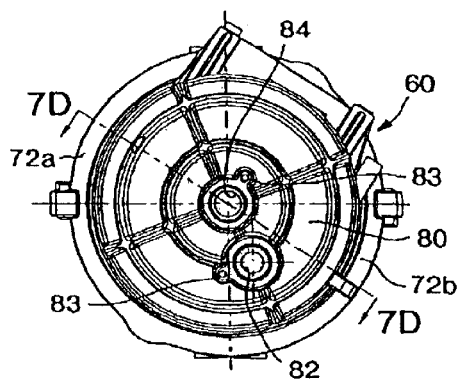
Figure 7B:
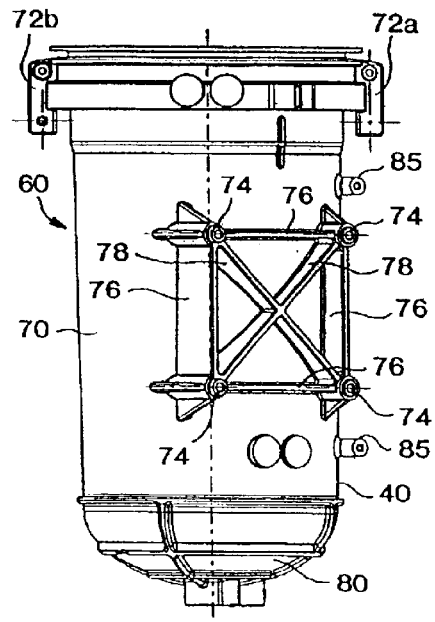
Figure 7D:
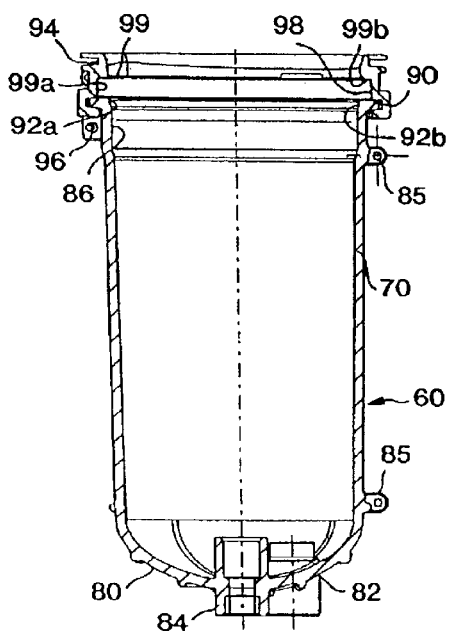

The individual components of filter subsystem 30 will now be described. Referring to FIGS. 7A–D, filter housing assembly 60 is shown. Filter housing assembly 60 includes a filter housing 70 and a pair of cooperating split rings 72a and 72b. Filter housing 70 has molded on its backside four threaded bosses 74. Supporting ribs 76 and 78 extend between and provide support to bosses 74. Filter housing 70 includes a lower domed end 80 having inlet and outlet conduits 82 and 84 formed therein. A pair of threaded bosses 83 are formed on the bottom of domed end 80 to receive fasteners which secure a portion of manifold assembly 40 to filter housing 70. Similarly, a pair of threaded bosses 85 are formed on the side of filter housing 70 to receive fasteners used to attach rear outer housing 14. At the top portion of filter housing 70 is interior seal mating mouth 86 and a retaining flange 90. Seal mating mouth 86 is sized to sealingly engage with O-ring 144 of filter cap assembly 64. Split rings 72a and 72b have radially inwardly extending grooves 92a and 92b. Fasteners 96 clamplingy secure split rings 72a and 72b about filter housing 70 with grooves 92a and 92b capturing retaining flange 90, as best seen in FIG. 7D. Blade receiving groove 98 extends the full circumference of filter assembly 66 and is formed between flange 90 and corresponding radially interior steps 99a and 99b formed in split rings 72a and 72b.

Figure 8A:
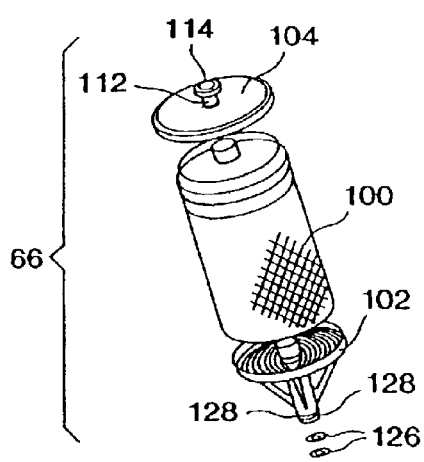
FIGS. 8A–D are, respectively, an exploded perspective view, a top plan view, a sectional view taken along line 8C—8C of FIG. 8B and a bottom plan view of the filter block assembly.
Figure 8C:
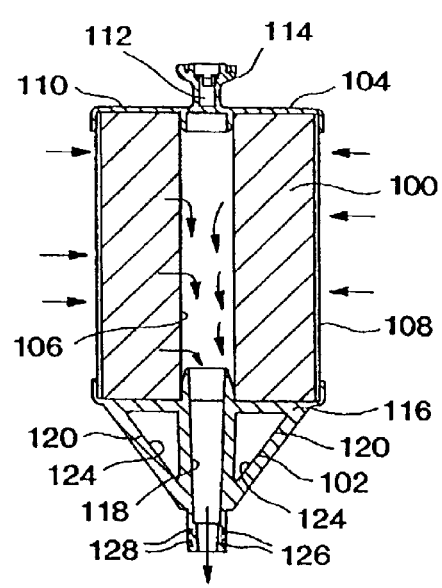
Figure 8B:
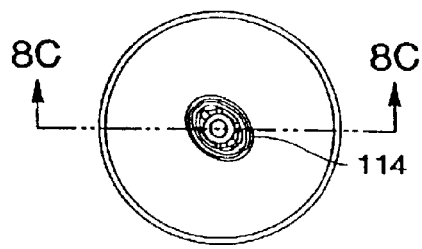
Figure 8D:
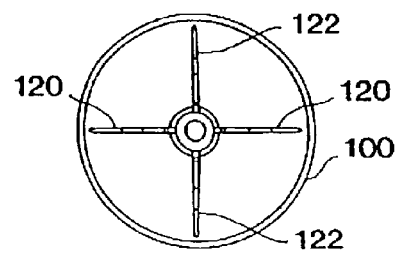

FIG. 8A shows an exploded view of filter assembly 66. A carbon filter block 100 is held between a filter bottom cap 102 and a filter top cap 104. Block filter 100 is annular and has inner and outer wraps 106 and 108, as best seen in FIG. 8C. Filter top cap 104 includes an end plate 110 with a post 112 and oval shaped grip disk 114. Oval shaped grip disk 114 allows filter assembly 66 to be easily grasped and pulled from filter housing assembly 60. Bottom cap 102 has an end plate 116, a central conduit 118 and two pair of triangular shaped supporting ribs 120 and 122 extending therebetween. Ribs 120 have triangular shaped openings 124 to provide weight reduction. A pair of O-rings 126 are retained in grooves 128 in central conduit 118 of end cap 102. Water flows radially inwardly from the outside of filter block 100 and exits through central conduit 118 during normal operation of WTS unit 10. Arrows indicate this desired direction of water flow in FIG. 8C. When filter assembly 66 is mounted within filter housing assembly 60, O-rings 126 seal between central conduit 118 and outlet conduit 84 (FIG. 7D) of filter housing assembly 60.

Figure 9:
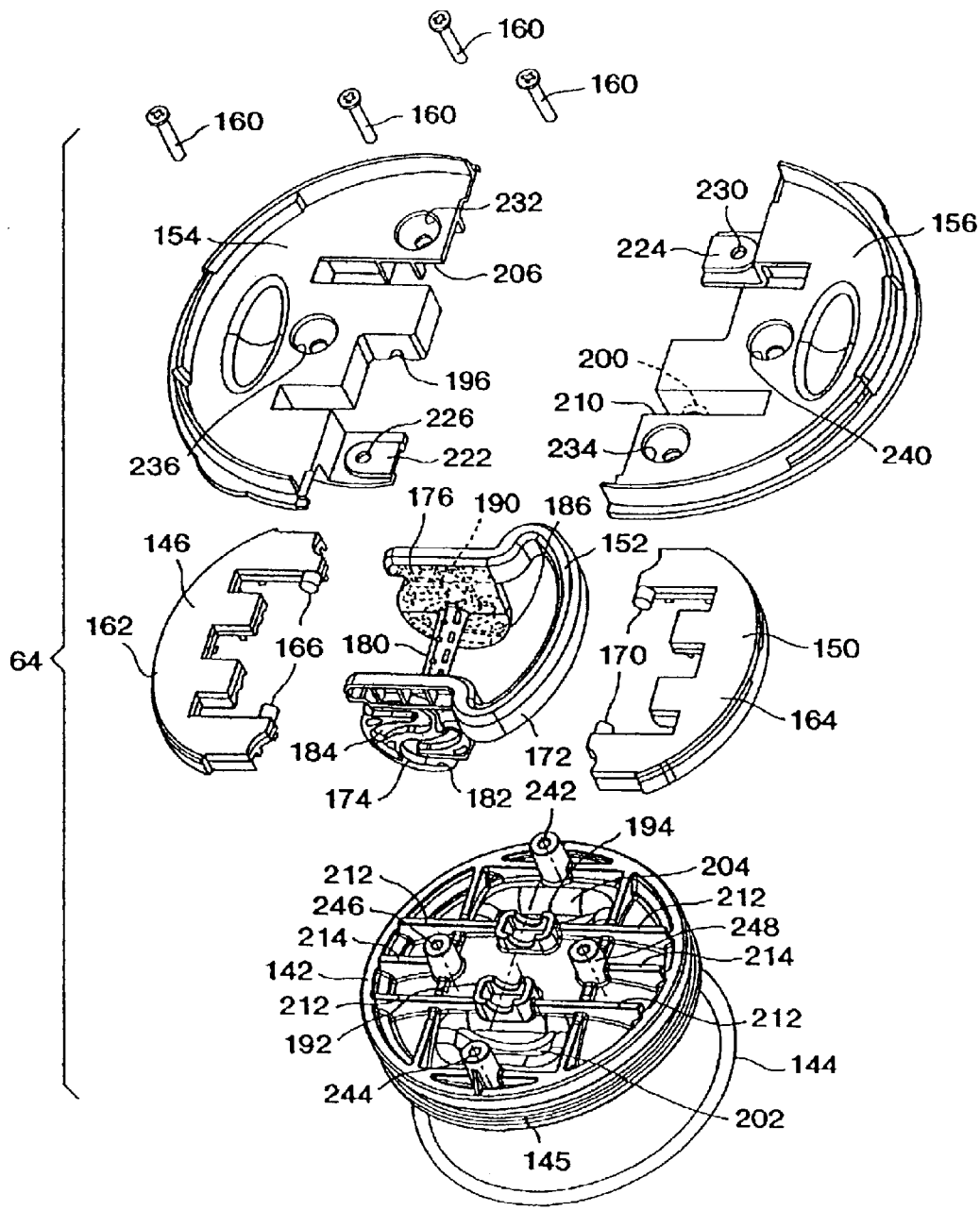
FIG. 9 is an enlarged exploded perspective view of a filter cap assembly.

FIG. 9 illustrates filter cap assembly 64 in an exploded perspective view. Elements comprising filter cap assembly 64 include filter housing cap 142, elastomeric O-ring 144, first and second cam lock blades 146 and 150, a handle 152, first and second cam lock retainers 154 and 156, and four fasteners 160. O-ring 144 is held in a groove 145 formed in the outer diameter of filter housing cap 142. Handle 152 and lock blades 146 and 150 are movably captured above filter housing cap 142 and below lock retainers 154 and 156 when filter cap assembly 64 is held together by fasteners 160. Handle 152 is retained to rotate between filter housing cap 142 and lock retainers 154 and 156. Handle 152 is attached to lock blades 146 and 150 such that blades 146 and 150 radially extend and retract in a horizontal plane as handle 152 is rotated downward and upward with respect to filter housing cap 142. When lock blades 146 and 150 are extended, they are adapted to lock into blade receiving groove 98 of filter housing assembly 60, as has been previously explained in regards to FIG. 6B.

Lock blades 146 and 150 are generally planar having respective arcuate engagement portions 162 and 164. Inboard extending pins 166 and 170 serve to connect with handle 152.

Handle 152 includes an arcuate grip portion 172, a pair of spaced apart ears 174 and 176 and an axle 180 connecting ears 174 and 176. Located on the outboard side of ears 174 and 176 are C-shaped cam tracks 182, 184 and 186, 190. Pins 166 and 170 of lock blades 146 and 150 cooperatively slide in cam tracks 182, 184, 186 and 190 to cause lock blades 146 and 150 to radially extend and retract as handle 152 is pivotally lowered and raised. Referring to FIG. 10C, when handle 152 is in its lowered position and pins 166 and 170 are disposed at the end of the tracks, pins 166 and 170 are maximally located from the centers of ears 174 and 176 as are lock blades 146 and 150. When grip portion 172 of handle 152 is raised, ears 174 and 176 rotate with pins 166 and 170 being cammed toward the center of ears 174 and 176 and adjacent the bight or mid-length portions of cam tracks 182, 184, 186 and 190. Lock blades 146 and 150 correspondingly travel radially inwardly into a retracted position as their pins 166 and 170 move or are cammed radially inwardly.

Referring to FIG. 9, axle 180 of handle 152 is retained to rotate in bearings formed by U-shaped yokes 192 and 194 disposed on the upper surface of filter housing cap 142 and cooperating U-shaped yokes 196 and 200 formed on the underside of cam lock retainers 154 and 156. Disk shaped recesses 202 and 204 are formed in filter housing cap 142 to accommodate ears 174 and 176. Similarly, slots 206 and 210 are formed in cam lock retainers 154 and 156 to facilitate the rotation of grip portion 172. Cam lock retainers 154 and 156 cooperate with the upper surface of filter housing cap 142 to guide lock blades 146 and 150 in planar movement between retracted and extended positions. Looking to FIG. 10D, outer and center guide ribs 212 and 214 are located atop filter housing cap 142 and cooperate with outer and center guide slots 216 and 220 formed on the underside of lock blades 146 and 150 to insure linear motion of lock blades 146 and 150 on filter housing cap 142. The camming action of handle 152 with pins 166 and 170 of lock blades 146 and 150 allows lock blades 146 and 150 to be easily retracted from blade receiving groove 98. Again, the problem of interacting threads "welding" together after long periods of non-use in a water treatment system unit is overcome in the present invention by using reciprocating lock blades 146 and 150 rather than a threaded connection between filter cap assembly 64 and filter housing assembly 60.

The distance from the center of axle 180 to grip portion 172 provides a much larger moment arm than the radial distance from the center of axle 180 to contact points where cam tracks 182, 184, 186 and 190 bear upon pins 166 and 170. Consequently, a user lifting or lowering handle 152 enjoys a substantial mechanical advantage in camming lock blades 146 and 150 radially inwardly or outwardly. Also, using disk shaped ears 174 and 176 with C-shaped cam tracks 182, 184, 186 and 190 allow pins 166 and 170 to move in a single horizontal plane even though cam tracks 182, 184, 186 and 190 move in a circular path as handle 152 is rotated. This allows lock blades 146 and 150 to be generally planar and the filter cap assembly 64 to be relatively compact in thickness.

Referring to FIG. 9, cam lock retainers 154 and 156 have respective tongues 222 and 224 with holes 226 and 230 therein. Similarly, countersunk holes 232, 234, 236 and 240 are formed in cam lock retainers 154 and 156. Corresponding threaded bosses 242, 244, 246 and 248 are located atop filter housing cap 142. As suggested in FIG. 9 when filter cap assembly 64 is fully assembled, threaded fasteners 160 are installed in countersunk holes 232, 234, 236 and 240 and are retained in threaded bosses 242, 244, 246 and 248. Holes 226 and 234 and holes 230 and 232 are coaxially aligned when cam lock retainers 154 and 156 are interlocked with one another.

In operation, filter cap assembly 64 is placed atop filter housing assembly 60 with handle 152 in an up position and lock blades 146 and 150 retracted radially inwardly. This allows lock blades 146 and 150 to retract from engagement with blade receiving groove 98 and to pass radially within split rings 72a and b of filter housing assembly 60. As filter cap assembly 64 is lowered and pressed into filter housing assembly 60, O-ring 144 slides into sealing engagement with seal mating mouth 86 of filter housing 70. A watertight seal is thus created between filter housing 70, O-ring 144 and filter housing cap 142. Once filter cap assembly 64 is pressed into filter housing assembly 60 with O-ring 144 effecting a seal with filter housing 70, filter cap assembly 64 must be locked in place. Handle 152 is rotated downwardly to be flush with filter housing cap 142 with lock blades 146 and 150 being cammed radially outwardly into engagement within blade retaining groove 98. O-ring 144 is compressively and sealingly captured between filter housing cap 142 and seal mating mouth 86 to maintain a seal between filter cap assembly 64 and filter housing assembly 60 thereby creating a closed pressure vessel. A generally single motion is thus effective in placing filter cap assembly 64 in position with filter housing assembly 60 and then lowering handle 152 to lock filter cap assembly 64 in place. The reverse is also true. Upon lifting handle 152, lock blades 146 and 150 are retracted and filter cap assembly 64 can be easily removed from seal mating mouth 86.

PC board 42, as seen in FIG. 3, includes a circuit board 250 upon which electronic components and circuitry are mounted. A female plug 252 is located near the base of circuit board 250 for receiving power from a male pin (not shown) on a connector cord of power supply 24. At the top of circuit board 250 a connector flange 254 which has a pair of C-shaped contacts 256 disposed on its front side. Another pair of contacts 260 are located near the base of circuit board 250 and are used to communicate with monitor 22 regarding the status of a UV lamp—i.e., is the lamp working.

Figure 11:
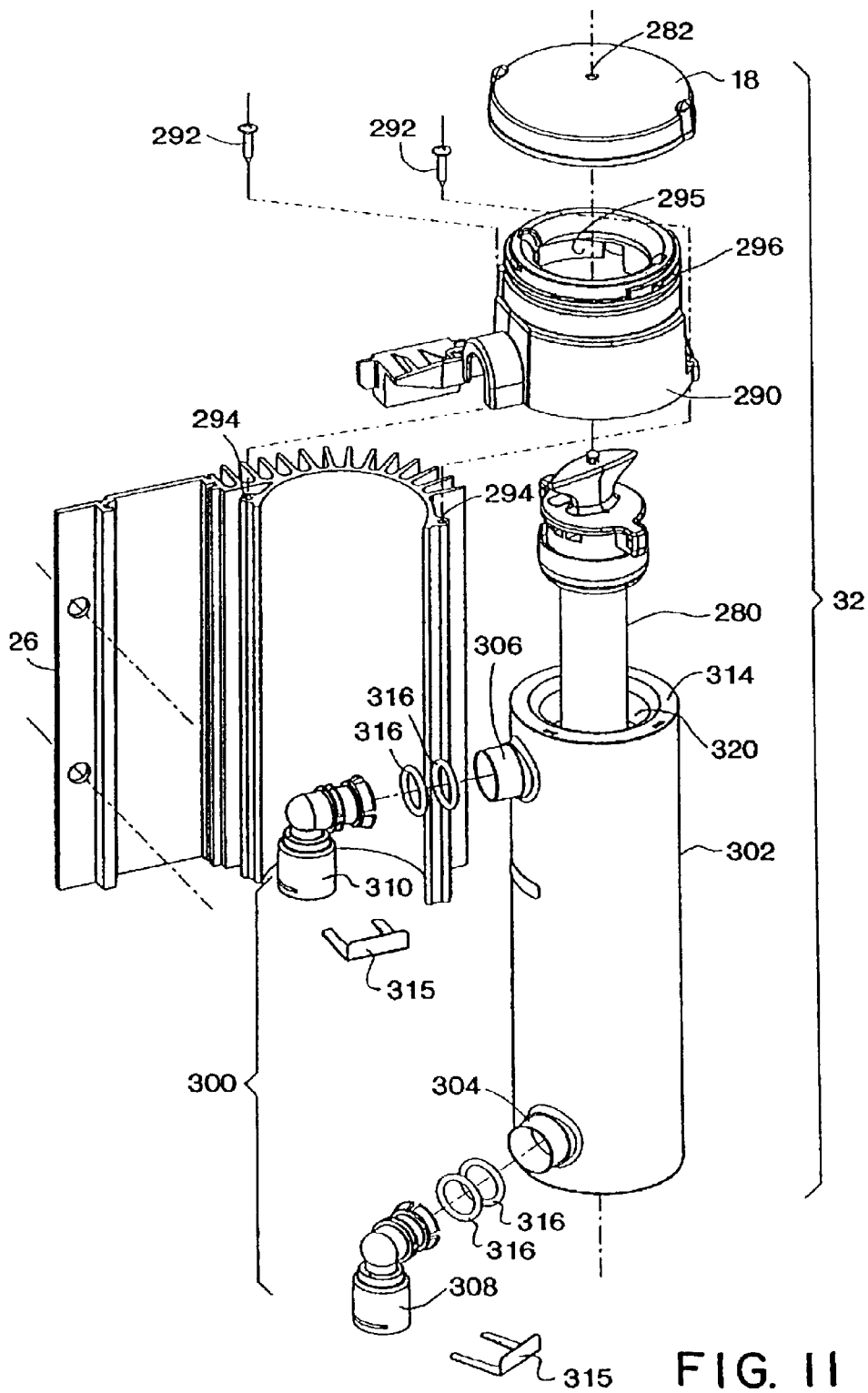
FIG. 11 is an exploded perspective view of a UV tank assembly and a heat dissipating support plate.

UV subsystem 32 is shown in exploded perspective view in FIG. 11 along with aluminum extrusion or support plate 26. Components of subsystem 32 include a UV lamp assembly 280, an electrical connector cap assembly 290, fasteners 292, bulb cover 18 and a UV tank assembly 300. Cap assembly 290 rests atop tank assembly 300 and is secured by fasteners 292 to openings 294 formed in support plate 26.

Figure 12A:
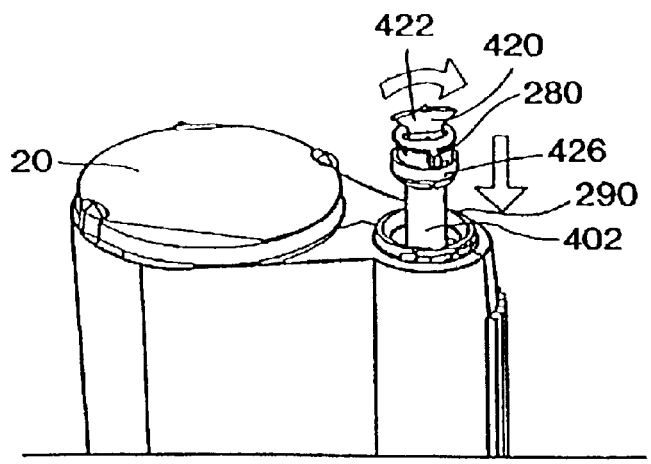
FIGS. 12A–C are a series of fragmentary perspective views of a UV lamp assembly being installed in a WTS unit.
Figure 12B:
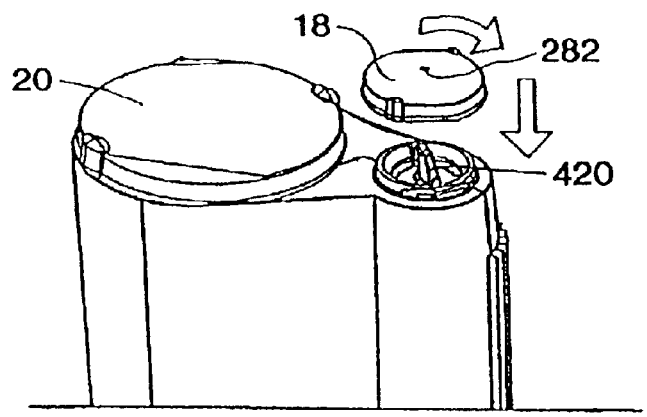
Figure 12C:
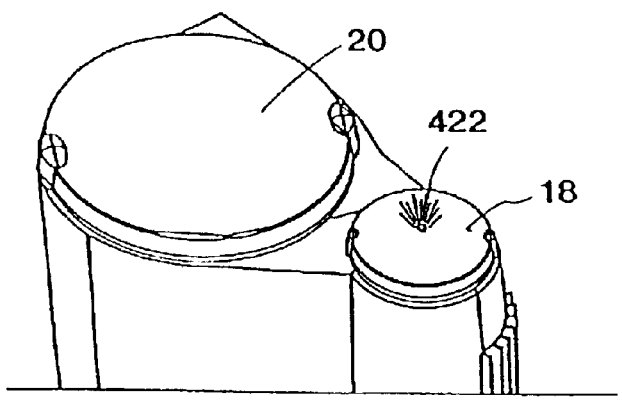

Lamp assembly 280 may then be installed in and removed from the combination of cap assembly 290 and tank assembly 300. Lamp assembly 280 fits within and electrically connects with electrical connector cap assembly 290 while fluidly sealing with tank assembly 300. Bulb cover 18 has a light pipe receiving aperture 282 centrally disposed therein. Threads 296 are formed on the exterior of cap assembly 290 for releasably retaining bulb cover 18. Support plate 26 is adapted to fit about and carry heat away from tank assembly 300 as well as PC board 42 (not shown in FIG. 11). Lamp assembly 280 must be properly installed in and sealed with tank assembly 300 and cap assembly 290, in a bayonet type installation, before cap assembly 290 can provide electrical power to lamp assembly 280. Proper installation prevents UV light from escaping from tank assembly 300 and cap assembly 290. Lamp assembly 280 is installed in cap assembly 290 and tank assembly 300 with a simple push and quarter turn of UV lamp assembly 280 into a bayonet mount 295 formed in cap assembly 290. This installation simultaneous effects a fluid sealing between lamp assembly 280 and tank assembly 300 and electrical connection between lamp assembly 280 and cap assembly 290, as suggested in FIGS. 12A–C.

Figure 13A:
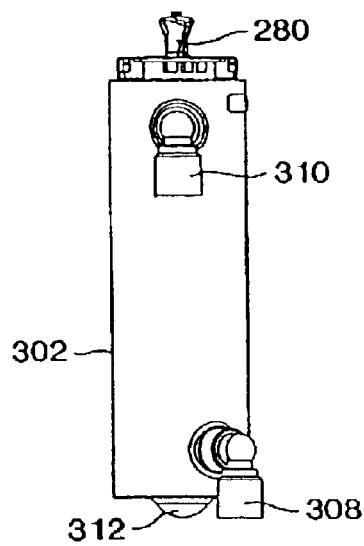
FIGS. 13A–E are, respectively, an elevational view, a top plan view, a sectional view taken along line 13C—13C of FIG. 13B, a bottom plan view and an enlarged fragmentary view from FIG. 13C of the UV lamp assembly.
Figure 13C:
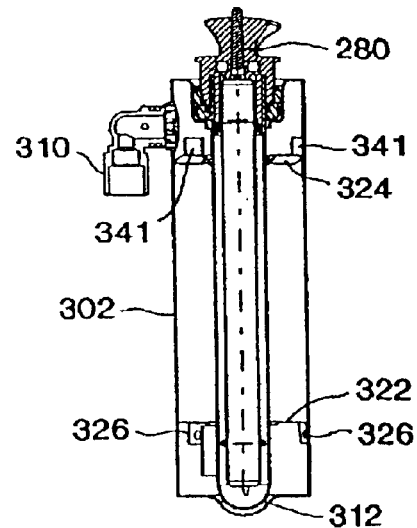
Figure 13B:
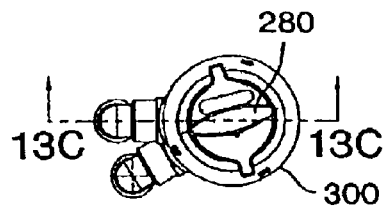
Figure 13D:
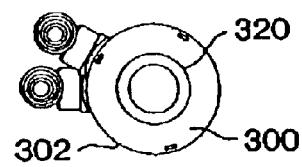
Figure 13E:
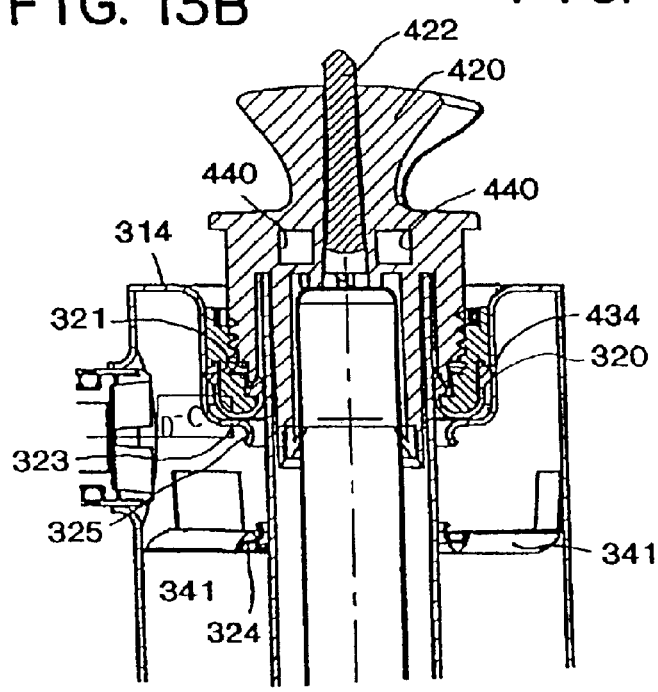
Figure 14:
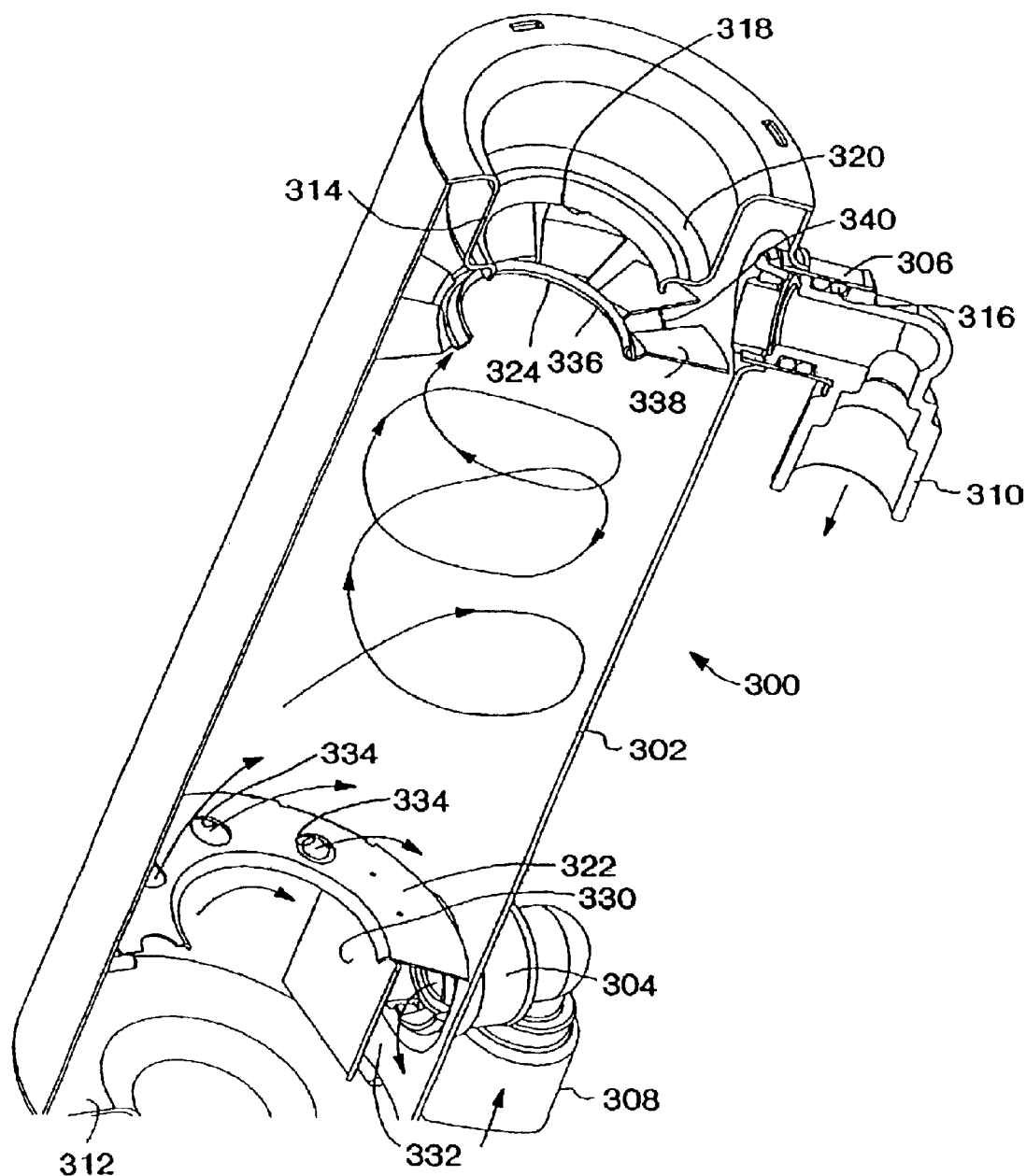
FIG. 14 is a fragmentary perspective view of the UV tank assembly.

Tank assembly 300 is shown in exploded view in FIG. 11, in combination with lamp assembly 280 in FIGS. 13A–E and individually in FIG. 14. Cap assembly 290 is not shown in FIGS. 13A–E for ease of viewing. Tank assembly 300 includes a cylindrical stainless steel main sleeve or tank 302 having inlet and outlet fittings 304 and 306 attached thereon, an inlet elbow 308, an outlet elbow 310, a bottom closed end plate 312 and a top annular cup-shaped end plate 314. Elbows 308 and 310 are affixed to fittings 304 and 306. Pairs of O-rings 316 are used to create seals between fittings 304 and 306 and elbows 308 and 310. Mounting clips 315 are placed into slots on elbows 308 and 310 to secure elbows 308 and 310 to manifold 40. A lamp receiving opening 318 is formed in top end plate 314. An annular seal surface 320 on end plate 314 is adapted to mate with a corresponding seal on lamp assembly 280 as best seen in FIG. 13E. End plate 314 also has a horizontal UV light block portion 323. A curled end portion 325 helps guide UV lamp assembly 280 during insertion and removal relative to tank assembly 300. Also, it reduces the chances of damage from any sharp stamped edges formed on top end plate 314 during manufacture.

Secured within tank 302 are a lower generally planar baffle plate 322 and an upper vaned baffle plate 324. Baffle plate 322 is annular and is welded to the interior of tank 302 using three attachment ears 326, as shown in FIG. 13C, which extend vertically downwardly along the wall of tank 302. Looking to FIG. 14, a diverter plate 330 is welded to baffle plate 322. Diverter plate 330 is positioned in front of fitting 304 to form a wedge shaped entrance chamber 332 and to cause incoming water to travel circumferentially. Diverter 330 also acts as a UV light block for lower elbow 308. A plurality of circular openings 334 are located in lower baffle plate 322 to allow water to travel toward upper baffle plate 324 in a spiral manner, as suggested by the arrows.

Upper baffle plate 324 is shown in FIGS. 13C, 14 and individually in FIGS. 15A–D. Upper baffle plate 324 has a circular hub 336 and tapered vanes 338. Vanes 338 are preferably angled at an angle alpha of 130 relative to the plane of circular hub 336. However, angles of between 5° and 45° will also induce acceptable circumferential or plug flow. Gaps 340 are formed between adjacent vanes 338 to allow water to flow therebetween. Three upstanding mounting ears 341 are used to secure baffle plate 324 to tank 302 through a welding operation. As tapered vanes 338 are angled upwardly in the direction of water flow, circumferential flow through gaps 340 is enhanced relative to using a planar baffle plate like first baffle plate 322 which has only generally planar openings 334 therein. Using a vaned baffle plate in the bottom of tank 302 has surprisingly shown less effectiveness in creating circumferential or plug water flow in tank assembly 300 relative to using a planar baffle plate 322 which has circular openings 334 therein. For maximum ease of manufacture and optimal creation of circumferential or plug flow, the combination of planar baffle plate 322 with circular openings 334 therein and vaned baffle plate 324 has proven to be very effective. This circumferential flow substantially eliminates laminar flow which allows different flow rates of water through the tank assembly 300. The enhanced plug flow of the present invention increases the minimal, relative to average, contact time of water exposed to UV light during operation of WTS unit 10. However, it is also within the scope of this invention that two or more of the vaned baffle plates could also be used to create the spiral or plug flow in a tank assembly.

Tank assembly 300 is constructed as follows. Tank 302 is cut to length from stainless steel tube stock. Openings are then stamped in sleeve or tank 302 to accommodate inlet fitting 304 and outlet fitting 306. Diverter plate 330 is spot welded to baffle plate 322. Baffle plate 322 is then plasma welded within tank 302 with diverter plate 330 positioned in front of the lower opening which will receive inlet fitting 304. Next, upper baffle plate 324 is plasma spot welded to tank 302. Inlet and outlet fittings 304 and 306 are swaged into engagement with the stamped openings in tank 302 and then plasma welded in place. Inlet and outlet elbows 308 and 310 are then attached to inlet and outlet fittings 304 and 306. Finally, lower end plate 312 and annular upper end plate 314 are plasma welded into place. The tank assembly is passivated to provide surface conditioning. This method of construction avoids the use of deep drawn materials, uses shallow drawn end plates and requires no machined parts. Thus tank assembly 300 provides a low cost but very effective, in terms of plug flow characteristics, UV tank assembly.

Electrical connector cap assembly 290 serves two general purposes. First, cap assembly 290 transfers electrical power from PC board 42 to UV lamp assembly 280. Second, cap assembly 290 uses a bayonet type connection to retain UV lamp assembly 280 mechanically in place relative to tank assembly 300. Cap assembly 290 rests upon tank assembly 300 and utilizing threaded fasteners 292 is attached to support plate 26, as suggested in FIG. 11. When UV lamp assembly 280 is properly held within cap assembly 290 and tank assembly 300, UV lamp assembly 280 is energized and UV light cannot escape from UV subsystem 32. Further, UV lamp assembly 280 also fluidly seals with tank assembly 300, as shown in FIG. 13E.

Cap assembly 290 is shown in FIGS. 16A–D. Looking to exploded view 16A, components include a plastic molded connector cap 342, a pre-mold 344, a lead frame 346 and a pair of clips 350. Lead frame 346 has upper and lower pairs of terminals 348 and 349 at its distal ends. Clips 350 each include curved elongate portions 352, intermediate arched contact portions 354 and end portions 356 and 358. Pre-mold 344 and lead frame 346 are captured within molded connector cap 342 during a molding operation which produces cap assembly 290, which is shown in its completed assembly in perspective view in FIG. 16B.

Figure 16A:
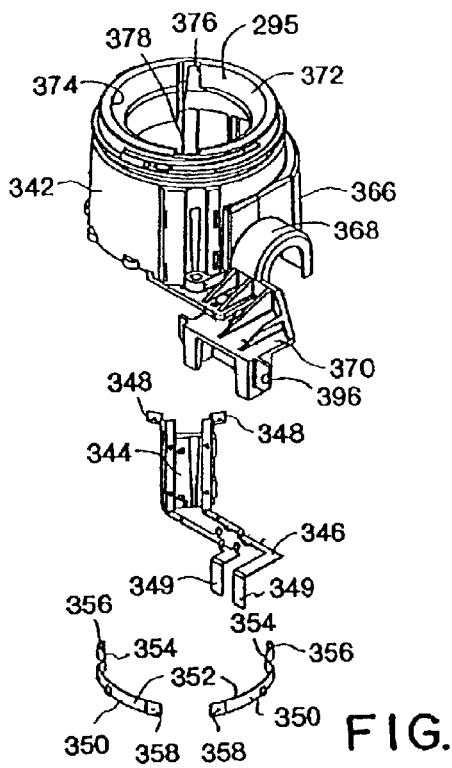
FIGS. 16A–D are an exploded perspective view, a perspective view, a bottom plan view and an inverted sectional view taken along line 16D—16D of FIG. 16C of an electrical connector cap assembly.
Figure 16B:
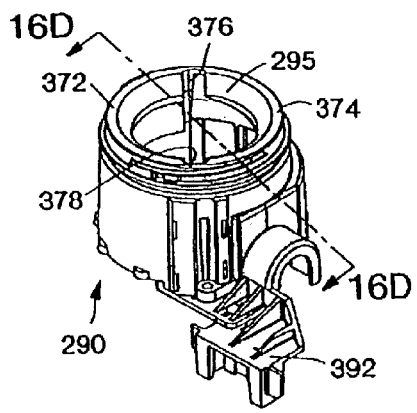
Figure 16C:
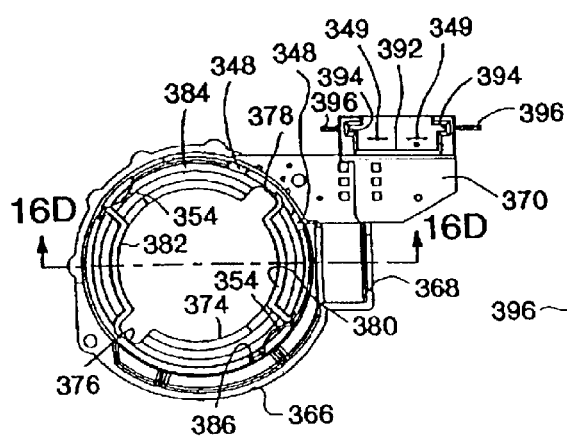
Figure 16D:
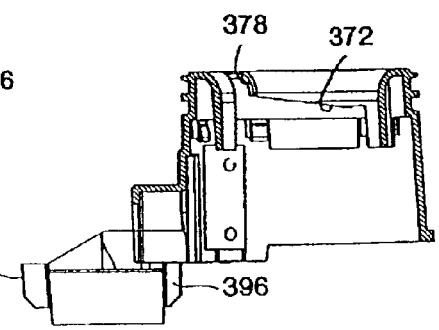

Connector cap 342 has a generally cylindrical main body 366, a tunnel portion 368 and an extension portion 370 molded about lead frame 346. A bayonet mount 295 is formed atop connection cap 342 to retain UV lamp assembly 280. Bayonet mount 295 comprises inwardly rolled flanges 372 and 374. Slots 376 and 378 are formed between rolled flanges 372 and 374. The inner edges of rolled flanges 372 and 374 taper downwardly as they extend away from slots 376 and 378 creating ramped surfaces. Flange 372 is shown in FIG. 16D tapering downwardly from slot 378. Formed on the inside of connector cap 342 are retaining clip walls 380, 382 and 384, as best seen in FIG. 16C. Curved elongate portions 352 and end portions 362 and 364 of clips 350 are retained by these clip walls 380, 382 and 384, as seen in FIG. 16C. Arched contact portions 354 are exposed on the interior of connector cap 342 and are circumferentially spaced from slots 376 and 378. Clip walls 380 and 382 serve as stops when lamp assembly 270 is bayonet mounted in cap assembly 290. After clips 350 are mounted behind walls 380, 382, and 384, terminals 348 of lead frame 346 are electrically connected to the end portions 358 of clips 350.

Terminals 349 are held in a U-shaped mounting pocket 392 formed in extension 370 of connector cap 342, as best seen in FIG. 16C. Interior slots 394 are sized in mounting pocket 392 to hold connector flange 254 of PC board 42. When mounting pocket 392 is slidably mounted over PC board 42, terminals 349 contacts are held within C-shaped clips 256 on PC board 42 (see FIG. 3). Outer flanges 396 are formed on mounting pocket 392 and are sized to be received in the upper portion of corresponding slots 574 formed in support plate 26 (see FIG. 19F). Tunnel portion 368 is sized to fit over outlet elbow 310 on tank assembly 300.

Figure 17A:
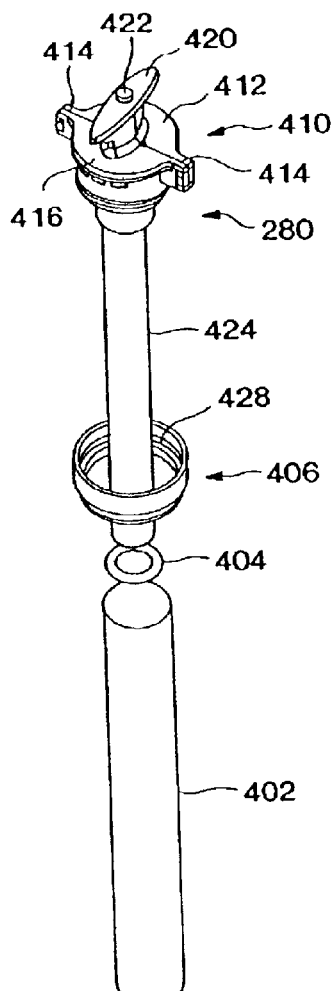
FIGS. 17A–D are an exploded perspective view, an elevational view, a top plan view and a sectional view of a lamp assembly taken along line 17D—17D of FIG. 17C.
Figure 17B:
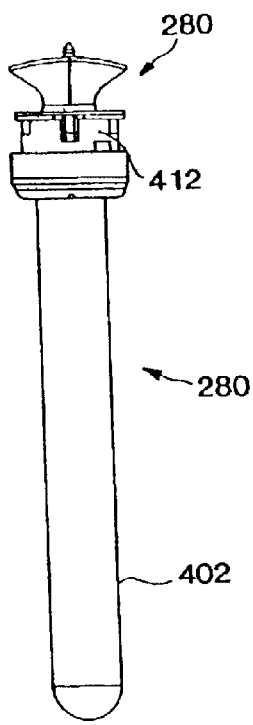
Figure 17D:
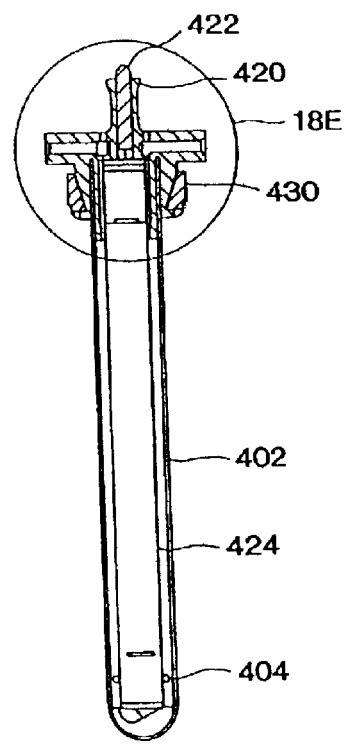
Figure 17C:
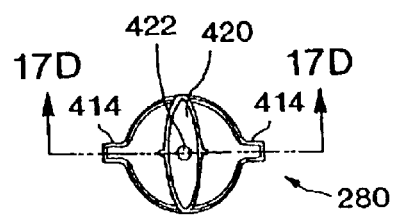

UV lamp assembly 280 is best seen in FIGS. 17A–D and 18A–B. Lamp assembly 280 includes a quartz sleeve 402, a bumper O-ring 404, a compression nut subassembly 406 and a bulb/connector subassembly 410. As best seen in FIG. 17A, subassembly 410 has a main molded body 412 including a pair of radially extending flanges 414, an annular hub 416, and a knob 420. An annular slot 418 is formed in hub 416 and receives the upper open end of quartz sleeve 402. At the lower end of hub 416 is formed an annular wedge portion 419 located adjacent compression nut subassembly 406. A light pipe 422 is held in a press-fit within an opening in knob 420. As shown, light pipe 422 is exposed to a UV bulb 424.

Compression nut subassembly 406 includes a nut 426 with internal threads 428 which are threadedly mountable to corresponding external threads 429 on hub 416. An annular elastomeric overmolded seal member 430 encompasses the lower portion of nut 426. In cross-section, seal member 430 is U-shaped having radially inboard and outboard beads 432 and 434. Inner radial seal bead 432 seals with quartz sleeve 402 and hub 416. As compression nut assembly 406 is threaded on hub 416, compression nut 426 bears upon annular wedge portion 419 creating a fluid tight seal therebetween. Outer radial bead 434 seals (see FIG. 13E) with seal surface 320 in the mouth of tank assembly 300 when UV lamp assembly 280 is bayonet mounted within cap assembly 290. An elastomeric gasket 408, V-shaped in cross section, is interposed between connector body 412 and bulb 424 to retain bulb 424.

Figure 18A:
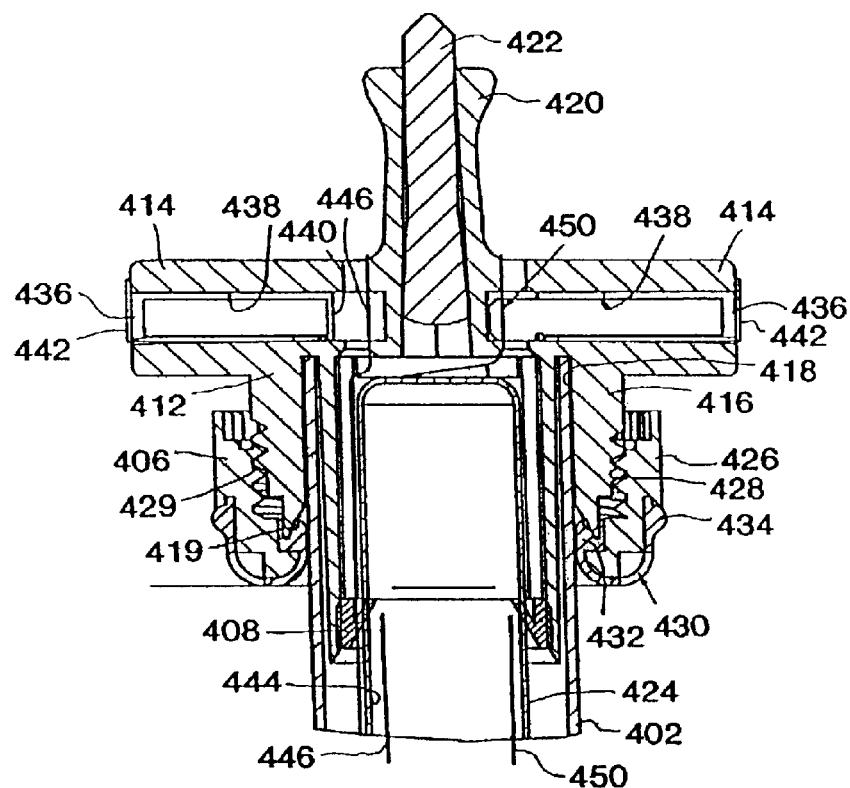
FIGS. 18A–B are an enlarged fragmentary view taken from FIG. 17D of the UV lamp assembly and a corresponding view from an alternative embodiment for a UV lamp assembly.
Figure 18B:
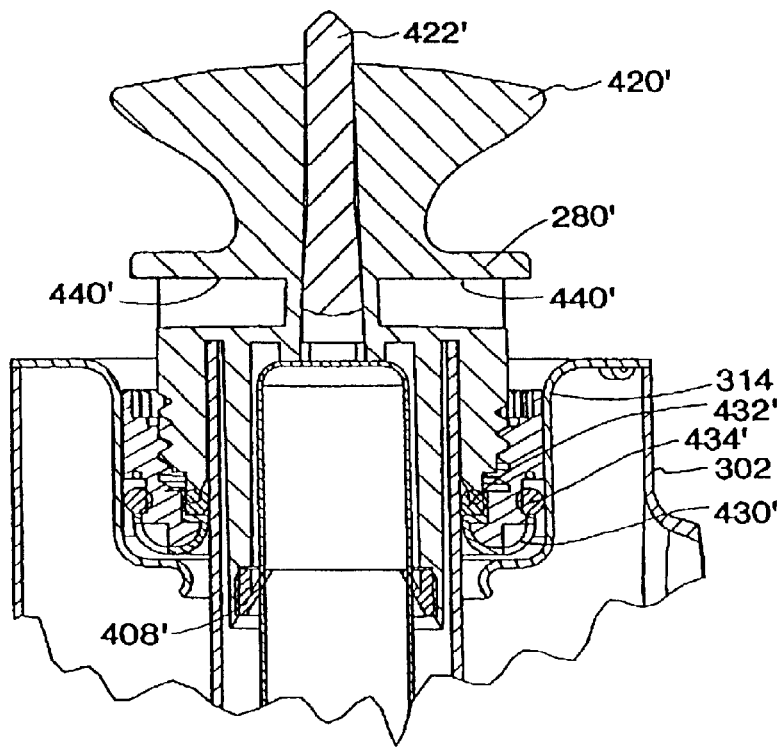

FIG. 18B shows an alternative embodiment for a UV lamp assembly 280' which is similar in design to UV lamp assembly 280 with the exception of compression nut 426. Rather than using elastomeric seal member 430 having inboard and outboard beads 432 and 434, a seal member 430' is used in conjunction with discrete O-rings 432' and 434'. L-shaped steps are formed in seal member 430' to hold O-rings 432' and 434' in place.

A pair of electrical terminals 436 is disposed within radially extending slots 438 formed in flanges 414. Terminals 436 are electrically connected to UV bulb 424 by way of filaments 446 and 450. Extending perpendicular to slots 438 are access slots 440 which allow access for filaments 446 and 450 to be soldered to respective terminals 436. Exposed radial end portions 442 on terminals 436 electrically connect with the arched contact portions 354 of clips 350 when UV lamp assembly 280 is bayonet mounted within cap assembly 290.

Referring to FIGS. 12A–C and FIGS. 16 and 18A, UV lamp assembly 280 is installed by removing bulb cover 18 and bayonet mounting UV lamp assembly 280 in cap assembly 290. Flanges 414, which carry terminals 436, are aligned with slots 376 and 378 in cap assembly 290. UV lamp assembly 280 is lowered into cap assembly 290 and tank assembly 300. Outer radial bead 434 of compression nut 406 comes into contact with seal surface 320 of tank assembly 300. Knob 420 is rotated 900 with flanges 414 bearing on the underside of rolled flanges 372 and 374 until striking retaining clip walls 380 and 384. At this time, arched contact portions 354 of clips, 350 of cap assembly 290 are in electrical communication with radial end portions 442 on terminals 436 on UV lamp assembly 280 thus energizing UV bulb 444. In turn, light pipe 422 is lit indicating to a user that UV lamp assembly 280 is properly installed and operating. Concurrently, UV lamp assembly 280 is locked in place by the bayonet mount 295 while sealing with seal surface 320 of tank assembly 300. Bulb cover 18 may then be mounted on the outside of cap assembly 290. Light pipe 422 extends through aperture 282 in bulb cover 18. Because light pipe 422 is part of the replacement UV lamp assembly 280, light pipe 422 is thus replaced with every change of UV lamp assembly 280. Discoloration of light pipe 422 due to exposure of high energy UV light is thus of only minor concern in this design of WTS unit 10.

Manifold assembly 40 is shown in FIGS. 19A–F. Manifold assembly 40 is comprised of a bottom manifold half 500 and a top manifold half 502 which includes a manifold pipe 504. Bottom and top manifold halves 500 and 502 are joined together to form a series of three conduits therebetween, which along with manifold pipe 504, place the various major subcomponents of WTS unit 10 in fluid communication with one another. These conduits include a manifold inlet conduit 506, a manifold outlet conduit 510 and a UV subsystem conduit 512.

Inlet conduit 506 connects between faucet diverter valve assembly 28 and filter subsystem 30. UV subsystem conduit 512 connects the outlet of filter subsystem 30 with the Inlet to UV subsystem 32. Manifold pipe 504 connects the outlet of UV subsystem 32 to water pipe assembly 34. Outlet conduit 506 returns water from water pipe assembly 34 to faucet diverter valve assembly 28.

Manifold inlet conduit 506 connects an inlet collet assembly 514 to a manifold nipple 516. Nipple 516 connects with inlet conduit 82 on filter assembly 66. As seen in FIG. 3, a duckbill valve assembly 518 is provided to connect between outlet conduit 84 of filter assembly 66 and a manifold nipple 520 of subsystem conduit 512. Duckbill valve assembly 518 prevents the backflow of water from UV lamp assembly 280 to filter assembly 66. UV subsystem conduit 512 extends between nipple 520 and manifold nipple 522. Nipple 522 attaches to inlet elbow 308 of UV tank assembly 300. A similar nipple 524 is formed on the upper free end of manifold pipe 504 which connects to outlet elbow 310. On the underside of manifold assembly 40 and at the other end of manifold pipe 504 is formed a nipple 528. Nipple 528 secures to an inlet on water pipe assembly 34. The outlet from water pipe assembly 34 is connected to a water pipe outlet nipple 530 on manifold 40. Nipple 530 serves as the inlet to outlet conduit 510. Three threaded bosses 534 are formed on the bottom of manifold assembly 40 to receive fasteners 610 (FIG. 20) which attach flow monitor assembly 16 to manifold 40.

Geometrically, manifold assembly 40 generally has a lower planar portion 536, a diagonal riser portion 540 and an upper planar portion 542. A UV subsystem circular retaining wall 538 on upper planar portion 542 helps center and retain tank assembly 300 when UV tank 302 is mounted atop manifold assembly 40. As filter subsystem 30 is greater in height than UV subsystem 32, utilizing this bi-planar manifold design allows for the existence of a spatial envelope 54 formed beneath upper planar portion 542 and above flow monitor assembly 16 in which water pipe assembly 34 resides. This biplanar manifold design allows WTS unit 10 to be compact in size, which is important on countertops of limited size. Also, as manifold assembly 40 is generally integral after being sonically welded together, no loose hoses are utilized in connecting subcomponents of WTS unit 10. Thus, an ordinary WTS unit 10 user can relatively easily replace subcomponents without changing any hoses. Manifold assembly 40 is threadedly secured by two bosses 544 to boss 83 on the bottom of filter housing 70 and at two mounting ears 546 to support plate 26.

Referring to FIGS. 19 E–F, heat dissipating support plate 26 has an arcuate portion 560 and a planar portion 562. Arcuate portion 560 is adapted to be juxtaposed with tank assembly 300 (FIG. 4). Radially extending fins 564 on support plate 26 provide a large surface area to dissipate heat into the atmosphere. Heat generated by UV lamp assembly 290 is conducted to sleeve or tank 302 and then to arcuate portion 560. Arcuate portion 560 passes the heat to fins 564 which readily give away heat to the atmosphere. Arcuate portion 560 and tank assembly 300 are juxtaposed for approximately 180°. It is envisioned that this area of contact could extend from between 45°–270°, depending on the amount of heat dissipation desired.

Figure 19E:
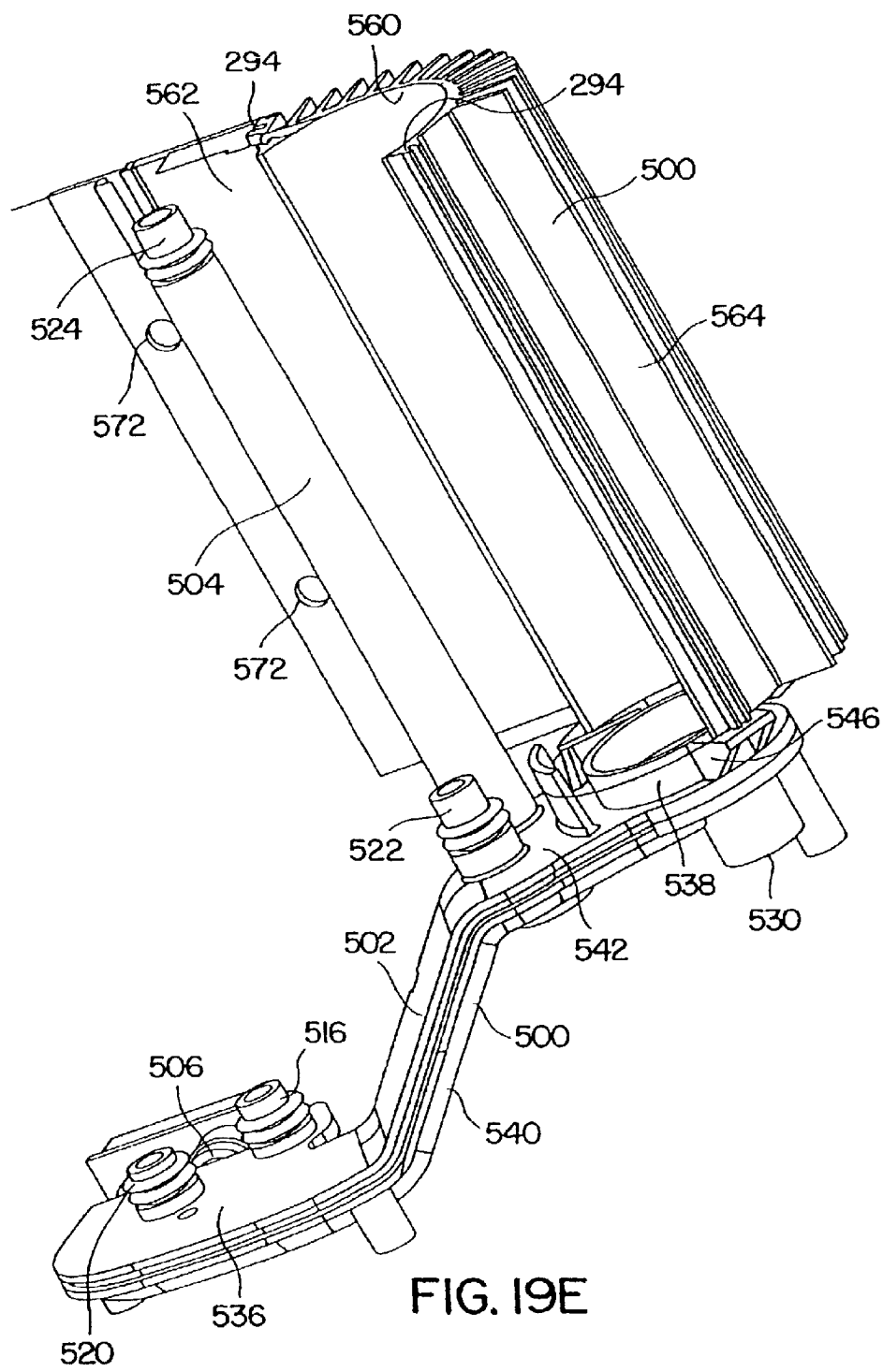
Figure 19F:
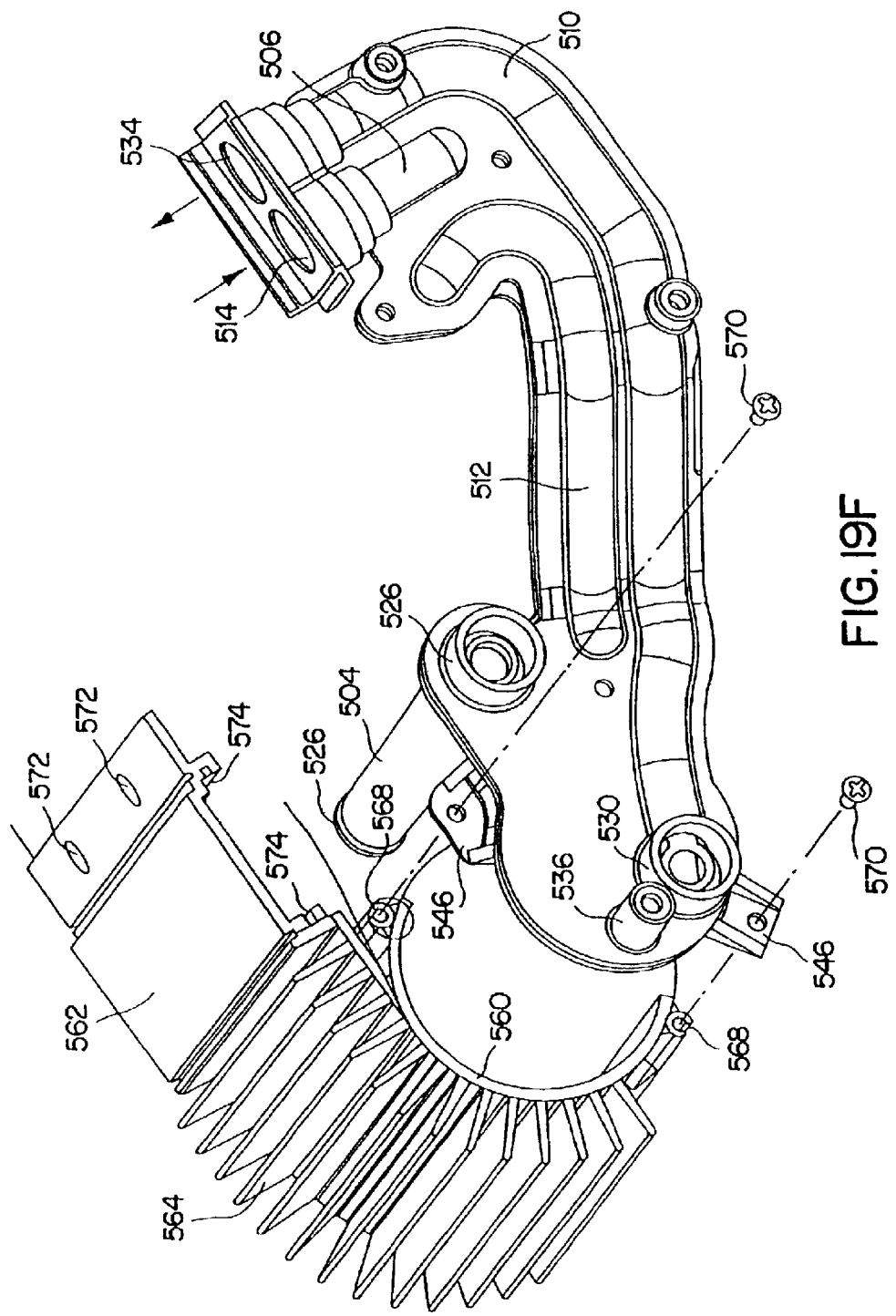

As shown in FIG. 19F, support plate 26 has a pair of apertures 568 for receiving threaded fasteners 570 to attach manifold 40. Support plate 26 also has a pair of openings 572 for receiving fasteners that also attach to a pair of threaded bosses 74 located on back of filter housing 70 (see FIG. 3) and also two vertically spaced corresponding openings in mounting bracket 44. A PC board-receiving slot 574 is formed in planar portion 562 to retain the vertical edges of PC board 42. Cap assembly 290 also is threadedly fastened by fasteners 292 to support plate 26 at two threaded openings 294 (FIG. 11). Finally, flanges 396 of cap assembly 290 (FIG. 16) are also retained by slot 574. Consequently, support plate 26 concurrently provides important structural support and heat dissipation capabilities to WTS unit 10.

Figure 20:
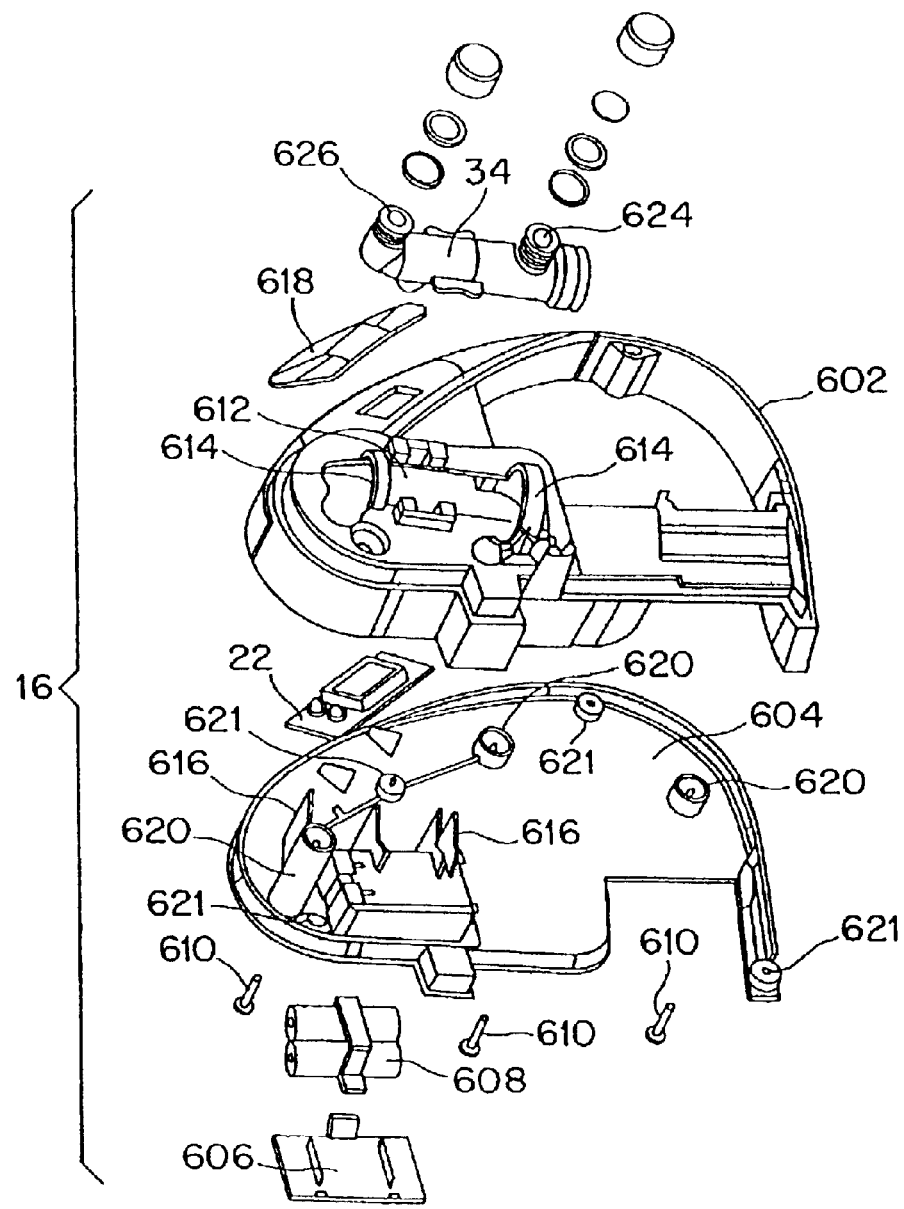
FIG. 20 is an exploded perspective view of a flow monitor assembly including a water pipe assembly.

Flow monitor assembly 16 is displayed in FIGS. 3, 4, and 20. As described previously, flow monitor assembly 16 serves as the base for WTS unit 10. Flow monitor assembly 16 includes a bottom housing 602, a bottom housing cover 604, a battery door 606, and a battery pack 608, fasteners 610, water pipe assembly 34 and monitor 22. Water pipe assembly 34 and monitor 22 are retained within bottom housing 602. A water pipe receiving opening 612 and retaining bands 614 are formed in bottom housing 602 to hold water pipe assembly 34. Similarly, four support ribs 616 on the top side of bottom housing cover 604 provide underneath support to monitor 22. Three fasteners 610 pass through three apertured bosses 620 in bottom housing cover 604 and are used to secure flow monitor assembly 16 to threaded bosses 534 of manifold assembly 40. Similar four other fasteners 610 passes through bosses 621 in bottom housing cover 604 to attach directly to threaded bosses (not shown) on the underside of bottom housing 602.

Water pipe assembly 34 has an inlet 624 and an outlet 626. Water flowing through water pipe assembly 34 turns a turbine which electronically sends water flow information to monitor 22. Inlet 624 receives water from manifold pipe nipple 526 and returns the water to nipple 530 of manifold outlet conduit 510 for discharge from WTS unit 10.

Monitor 22 is in electronic communication with UV lamp assembly 280, water pipe assembly 34 and battery pack 608. Status information regarding WTS unit 10 is displayed by monitor 22. An overlay label 618 covers monitor 22. Because of the unique bi-planar design of manifold assembly 40, envelope 54 is created beneath upper planar portion 542 of manifold assembly 40. Envelope 54 is best displayed in FIG. 4.

Front and rear outer housings 12 and 14 form a clam shell housing which clamps about the other major subcomponents of WTS unit 10. Referring to FIG. 3, apertured bosses 650 on the left rear side of rear outer housing 14 allows fasteners (not shown) to attach to corresponding bosses 652 in front outer housing 12. Looking to FIG. 2, apertured bosses 654 allow fasteners to be secured to threaded bosses 85 (FIG. 7B) formed on filter housing 70.

While in the foregoing specification this invention has been described in relation to certain preferred embodiments thereof, and many details have been set forth for the purpose of illustration, it will be apparent to those skilled in the art that the invention is susceptible to alteration and that certain other details described herein can vary considerably without departing from the basic principles of the invention.

What is claimed:

1. A point-of-use water treatment system comprising:

an untreated water inlet;

a filter subsystem;

a subsystem;

a treated water outlet;

a housing; and a manifold for fluidly connecting said inlet, said filter subsystem, said subsystem and said outlet, said manifold including a bottom manifold portion and a top manifold portion, said bottom and top portions cooperating to define a plurality of flow conduits fluidly interconnecting said inlet, said filter subsystem, said subsystem and said outlet, said manifold including a lower portion extending along a lower plane, an upper portion extending along an upper plane and a riser portion extending between said lower plane and said upper plane, said upper portion and said housing cooperatively defining a spatial envelope.

2. The water treatment system of claim 1 wherein said manifold includes an inlet conduit fluidly connecting said inlet and said filter subsystem;

a subsystem conduit fluidly connecting said filter subsystem and said subsystem; and an outlet conduit fluidly connecting said subsystem and said outlet.

3. The water treatment system of claim 2 wherein said manifold includes a biplanar configuration with a lower portion extending along a lower plane, an upper portion extending along an upper plane and a riser portion extending between said lower plane and said upper plane, said manifold defining a spatial envelope beneath said upper portion; and further comprising a flow monitor assembly, said flow monitor assembly disposed within said spatial envelope defined beneath said upper portion.

4. The water treatment system of claim 3 wherein said top portion and said bottom portion are intersecured by sonic welding.

5. A point-of-use water treatment system comprising:

a housing;

an untreated water inlet contained within said housing;

a filter subsystem contained within said housing;

a subsystem contained within said housing;

a treated water outlet contained within said housing;

a manifold for fluidly connecting said inlet, said filter subsystem, said subsystem and said outlet, said manifold including a bottom manifold portion and a top manifold portion, said manifold including a lower portion extending along a lower plane, an upper portion extending along an upper plane and a riser portion extending between said lower plane and said upper plane, said upper portion and said housing cooperatively defining a spatial envelope; and a flow monitor assembly disposed within said spatial envelope.

6. The water treatment system of claim 5 wherein said bottom and top portions cooperating to define a plurality of flow conduits fluidly interconnecting said inlet, said filter subsystem, said subsystem and said outlet.

7. The water treatment system of claim 6 wherein said manifold includes:

an inlet conduit fluidly connecting said inlet and said filter subsystem;

a subsystem conduit fluidly connecting said filter subsystem and said subsystem; and an outlet conduit fluidly connecting said subsystem and said outlet.

8. The water treatment system of claim 7 wherein said top portion and said bottom portion are intersecured by sonic welding and wherein said subsystem is a UV subsystem.

* * * * *